United States Patent
Sela et al.

(10) Patent No.: US 10,278,787 B2
(45) Date of Patent: *May 7, 2019

(54) PATIENT REFERENCE TOOL FOR RAPID REGISTRATION

(71) Applicant: SYNAPTIVE MEDICAL (BARBADOS) INC., Bridgetown (BB)

(72) Inventors: Gal Sela, Toronto (CA); Dorothy Lui, Toronto (CA); Kirusha Srimohanarajah, Toronto (CA); Thanh Vinh Vuong, Toronto (CA)

(73) Assignee: SYNAPTIVE MEDICAL (BARBADOS) INC., Bridgetown (BB)

(*) Notice: Subject to any disclaimer, the term of this patent is extended or adjusted under 35 U.S.C. 154(b) by 0 days.

This patent is subject to a terminal disclaimer.

(21) Appl. No.: 15/518,312

(22) PCT Filed: Jul. 31, 2015

(86) PCT No.: PCT/CA2015/050729
§ 371 (c)(1),
(2) Date: Apr. 11, 2017

(87) PCT Pub. No.: WO2016/058088
PCT Pub. Date: Apr. 21, 2016

(65) Prior Publication Data
US 2017/0239015 A1    Aug. 24, 2017

(30) Foreign Application Priority Data
Oct. 14, 2014 (WO) ................ PCT/CA2014/050987

(51) Int. Cl.
*A61B 90/00* (2016.01)
*A61B 46/10* (2016.01)
(Continued)

(52) U.S. Cl.
CPC .............. *A61B 90/39* (2016.02); *A61B 5/064* (2013.01); *A61B 34/20* (2016.02); *A61B 46/10* (2016.02);
(Continued)

(58) Field of Classification Search
CPC .. A61B 2017/00902; A61B 2034/2048; A61B 2034/2051; A61B 2034/2055;
(Continued)

(56) References Cited

U.S. PATENT DOCUMENTS 5,368,030 A    11/1994 Zinreich et al.
6,333,971 B2   12/2001 McCrory et al.
(Continued)

FOREIGN PATENT DOCUMENTS

WO    WO20131144 A2    8/2013

*Primary Examiner* — Christopher L Cook
(74) *Attorney, Agent, or Firm* — Ridout & Maybee LLP

(57) ABSTRACT

An apparatus is provided that is at least partially visible by both a three dimensional (3D) scanner system of a medical navigation system and a tracking system of the medical navigation system. The apparatus includes a rigid member, a plurality of identifiable features attached to the rigid member and visible by the tracking system, a distinct identifiable portion visible by the 3D scanner system, and a connector mechanism attached to the rigid member to connect the apparatus to a location. The apparatus is in a field of view of the 3D scanner system and the tracking system within a timeframe of the 3D scan.

23 Claims, 18 Drawing Sheets

(51) Int. Cl.
  *A61B 34/20* (2016.01)
  *A61B 5/06* (2006.01)
  *A61B 17/00* (2006.01)
  *A61B 50/13* (2016.01)
  *A61B 90/10* (2016.01)

(52) U.S. Cl.
  CPC ..... *A61B 50/13* (2016.02); *A61B 2017/00902* (2013.01); *A61B 2034/2048* (2016.02); *A61B 2034/2051* (2016.02); *A61B 2034/2055* (2016.02); *A61B 2034/2057* (2016.02); *A61B 2034/2063* (2016.02); *A61B 2034/2072* (2016.02); *A61B 2090/103* (2016.02); *A61B 2090/3945* (2016.02); *A61B 2090/3962* (2016.02); *A61B 2090/3979* (2016.02); *A61B 2090/3983* (2016.02); *A61B 2090/3991* (2016.02); *A61B 2090/3995* (2016.02)

(58) Field of Classification Search
  CPC .... A61B 2034/2057; A61B 2034/2063; A61B 2034/2072; A61B 2090/103; A61B 2090/3945; A61B 2090/3962; A61B 2090/3979; A61B 2090/3983; A61B 2090/3991; A61B 2090/399161
  See application file for complete search history.

(56) References Cited

U.S. PATENT DOCUMENTS

| | | | |
|---|---|---|---|
| 6,675,040 B1* | 1/2004 | Cosman | G06T 3/00 600/427 |
| 2009/0317002 A1* | 12/2009 | Dein | A61B 19/0256 382/224 |
| 2011/0069867 A1* | 3/2011 | Buehner | A61B 90/39 382/103 |
| 2011/0166446 A1 | 7/2011 | Whitmore, III et al. | |
| 2012/0059244 A1 | 3/2012 | McClelland et al. | |
| 2012/0184839 A1 | 7/2012 | Woerlein | |
| 2013/0331686 A1 | 12/2013 | Freysinger et al. | |
| 2014/0121500 A1* | 5/2014 | Geier | A61C 8/0001 600/424 |
| 2015/0164606 A1* | 6/2015 | Jacobs | A61B 19/5244 606/1 |
| 2015/0282735 A1* | 10/2015 | Rossner | A61B 5/064 600/424 |

* cited by examiner

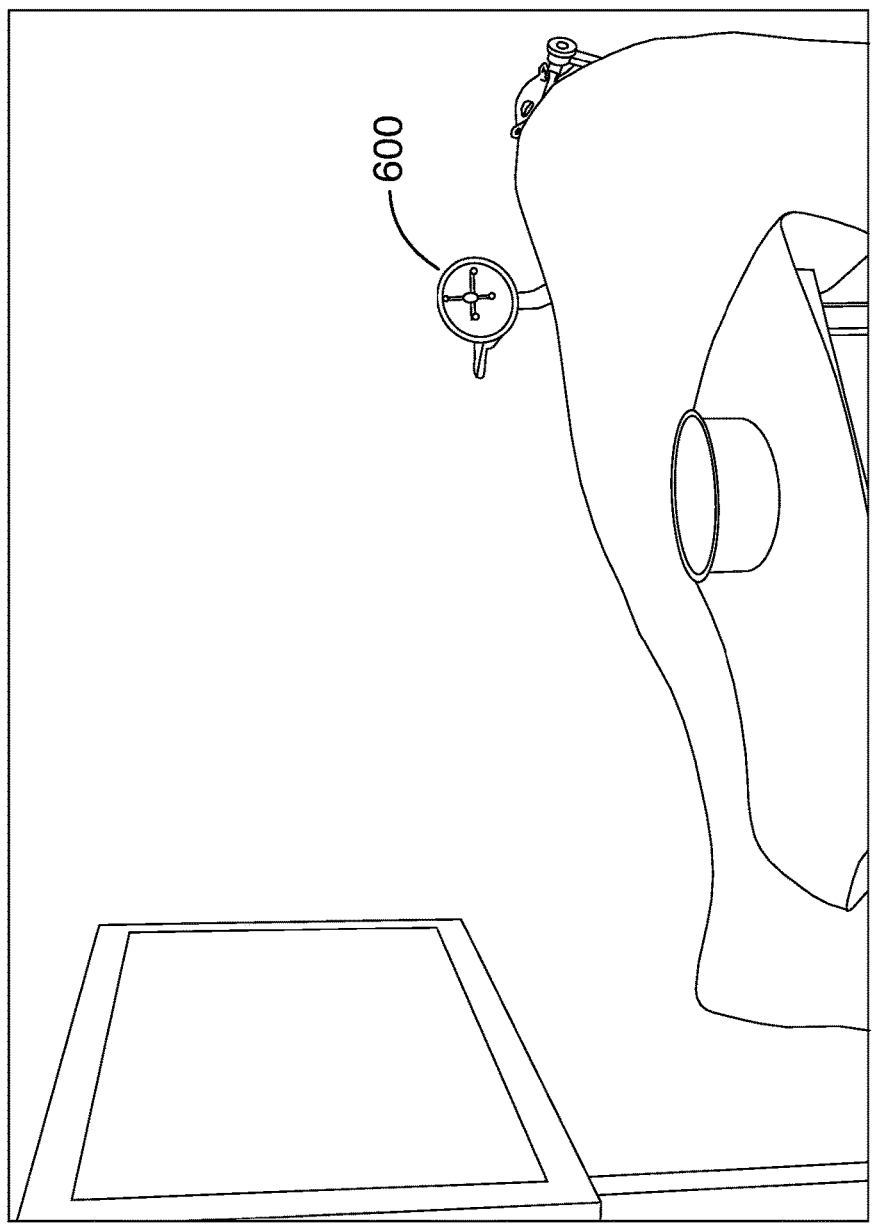

PATIENT REFERENCE TOOL FOR RAPID REGISTRATION

CROSS REFERENCE TO RELATED APPLICATIONS

The present disclosure claims priority to PCT Patent Application No. PCT/CA2014/050987 filed on Oct. 14, 2014, the entirety of which is hereby incorporated by reference.

TECHNICAL FIELD

The present disclosure is generally related to image guided medical procedures, and more specifically to a patient reference tool for rapid registration.

BACKGROUND

The present disclosure is generally related to image guided medical procedures using a surgical instrument, such as a fibre optic scope, an optical coherence tomography (OCT) probe, a micro ultrasound transducer, an electronic sensor or stimulator, or an access port based surgery.

In the example of a port-based surgery, a surgeon or robotic surgical system may perform a surgical procedure involving tumor resection in which the residual tumor remaining after is minimized, while also minimizing the trauma to the intact white and grey matter of the brain. In such procedures, trauma may occur, for example, due to contact with the access port, stress to the brain matter, unintentional impact with surgical devices, and/or accidental resection of healthy tissue. A key to minimizing trauma is ensuring that the spatial reference of the patient as understood by the surgical system is as accurate as possible.

FIG. 1 illustrates the insertion of an access port into a human brain, for providing access to internal brain tissue during a medical procedure. In FIG. 1, access port 12 is inserted into a human brain 10, providing access to internal brain tissue. Access port 12 may include such instruments as catheters, surgical probes, or cylindrical ports such as the NICO BrainPath. Surgical tools and instruments may then be inserted within the lumen of the access port in order to perform surgical, diagnostic or therapeutic procedures, such as resecting tumors as necessary. The present disclosure applies equally well to catheters, DBS needles, a biopsy procedure, and also to biopsies and/or catheters in other medical procedures performed on other parts of the body.

In the example of a port-based surgery, a straight or linear access port 12 is typically guided down a sulci path of the brain. Surgical instruments would then be inserted down the access port 12.

Optical tracking systems, used in the medical procedure, track the position of a part of the instrument that is within line-of-site of the optical tracking camera. These optical tracking systems also require a reference to the patient to know where the instrument is relative to the target (e.g., a tumour) of the medical procedure.

In the field of medicine, imaging and image guidance are a significant component of clinical care. From diagnosis and monitoring of disease, to planning of the surgical approach, to guidance during procedures and follow-up after the procedure is complete, imaging and image guidance provides effective and multifaceted treatment approaches, for a variety of procedures, including surgery and radiation therapy. Targeted stem cell delivery, adaptive chemotherapy regimes, and radiation therapy are only a few examples of procedures utilizing imaging guidance in the medical field.

Advanced imaging modalities such as Magnetic Resonance Imaging ("MRI") have led to improved rates and accuracy of detection, diagnosis and staging in several fields of medicine including neurology, where imaging of diseases such as brain cancer, stroke, Intra-Cerebral Hemorrhage ("ICH"), and neurodegenerative diseases, such as Parkinson's and Alzheimer's, are performed. As an imaging modality, MRI enables three-dimensional visualization of tissue with high contrast in soft tissue without the use of ionizing radiation. This modality is often used in conjunction with other modalities such as Ultrasound ("US"), Positron Emission Tomography ("PET") and Computed X-ray Tomography ("CT"), by examining the same tissue using the different physical principals available with each modality. CT is often used to visualize boney structures and blood vessels when used in conjunction with an intra-venous agent such as an iodinated contrast agent. MRI may also be performed using a similar contrast agent, such as an intra-venous gadolinium based contrast agent which has pharmaco-kinetic properties that enable visualization of tumors and break-down of the blood brain barrier. These multi-modality solutions can provide varying degrees of contrast between different tissue types, tissue function, and disease states. Imaging modalities can be used in isolation, or in combination to better differentiate and diagnose disease.

In neurosurgery, for example, brain tumors are typically excised through an open craniotomy approach guided by imaging. The data collected in these solutions typically consists of CT scans with an associated contrast agent, such as iodinated contrast agent, as well as MRI scans with an associated contrast agent, such as gadolinium contrast agent. Also, optical imaging is often used in the form of a microscope to differentiate the boundaries of the tumor from healthy tissue, known as the peripheral zone. Tracking of instruments relative to the patient and the associated imaging data is also often achieved by way of external hardware systems such as mechanical arms, or radiofrequency or optical tracking devices. As a set, these devices are commonly referred to as surgical navigation systems.

Three dimensional (3D) sensor systems are increasingly being used in a wide array of applications, including medical procedures. These sensor systems determine the shape and/or features of an object positioned in a scene of the sensor system's view. In recent years, many methods have been proposed for implementing 3D modeling systems that are capable of acquiring fast and accurate high resolution 3D images of objects for various applications.

Triangulation based 3D sensor systems and methods typically have one or more projectors as a light source for projecting onto a surface and one or more cameras at a defined, typically rectified relative position from the projector for imaging the lighted surface. The camera and the projector therefore have different optical paths, and the distance between them is referred to as the baseline. Through knowledge of the baseline distance as well as projection and imaging angles, known geometric/triangulation equations are utilized to determine distance to the imaged object. The main differences among the various triangulation methods known in the art lie in the method of projection as well as the type of light projected, typically structured light, and in the process of image decoding to obtain three dimensional data.

A 3D sensor system may be contemplated as a novel extension of a surgical navigation systems. One popular triangulation based 3D sensor system is created by Mantis Vision, which utilizes a single frame structured light active triangulation system to project infrared light patterns onto an environment. To capture 3D information, a projector overlays an infrared light pattern onto the scanning target. Then a digital camera and a depth sensor, synched to the projector, captures the scene with the light reflected by the object for at least the timeframe of one frame of the 3D scan. The technology works even in complete darkness, since it includes its own illumination; in bright environments the quality of the resulting image depends on the hardware used.

During a medical procedure, navigation systems require a registration to transform between the physical position of the patient in the operating room and the volumetric image set (e.g., MRI/CT) being navigated to. Conventionally, this registration is done to the position of a reference tool, which is visible by the tracking system and stays fixed in position and orientation relative to the patient throughout the procedure.

This registration is typically accomplished through correspondence touch points (e.g., either fiducial or anatomic points). Such an approach to registration has a number of disadvantages, including requiring fiducials to be placed before scans, requiring points to be identified, providing for a limited number of points, touch point collection is subject to user variability, and the physical stylus used for collecting the points can deform or deflect patient skin position. Another conventional approach to collecting the touch points includes performing a surface tracing of the patient drawn as a line which is matched to the image set surface contour using either a stylus pointer or a laser pointer. Such an approach to registration has a number of disadvantages, including providing for a limited number of points, and the physical stylus can deform or deflect patient skin position. Yet another conventional approach to collecting the touch points includes using a mask, which requires a high level of operator training and is operator dependent. This approach also provides only a limited number of points.

Other common limitations of the conventional approaches to registration discussed above include a stylus that needs to remain visible to the tracking system, which may not necessarily be possible depending on a patient's surgical position or may introduce surgical restrictions that need to be accounted in planning, and error accumulation where touch point or tracing collection is of low quality resulting in error propagation through subsequent steps of the registration. Further, using the conventional methods, if registration is lost, re-registration is difficult to be completed again during the surgical procedure.

Therefore, there is a need for an improved system and method for mapping navigation space to patient space in a medical procedure.

SUMMARY

One aspect of the present disclosure provides an apparatus that is at least partially visible by both a three dimensional (3D) scanner system of a medical navigation system and a tracking system of the medical navigation system. The apparatus includes a rigid member, a plurality of identifiable features attached to the rigid member and visible by the tracking system, a distinct identifiable portion visible by the 3D scanner system, and a connector mechanism attached to the rigid member to connect the apparatus to a location. The apparatus is in a field of view of the 3D scanner system and the tracking system within a timeframe of the 3D scan.

Another aspect of the present disclosure provides a patient reference device for use during a medical procedure. The patient reference device includes a housing having a back side and a front side, a plurality of tracking markers attached to the front side of the housing, and a three dimensional indicator formed on the front side of the housing. The housing extends around the at least three tracking markers and beyond a horizontal plane defined by tops of the at least three tracking markers. The housing terminates at a substantially continuous edge. A sterile cover is attached to the substantially continuous edge of the housing for covering the housing and the tracking markers.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIG. 9A is a perspective drawing illustrating an environmental context of the exemplary patient reference device shown in FIG. 6;

DETAILED DESCRIPTION

Figure 1:
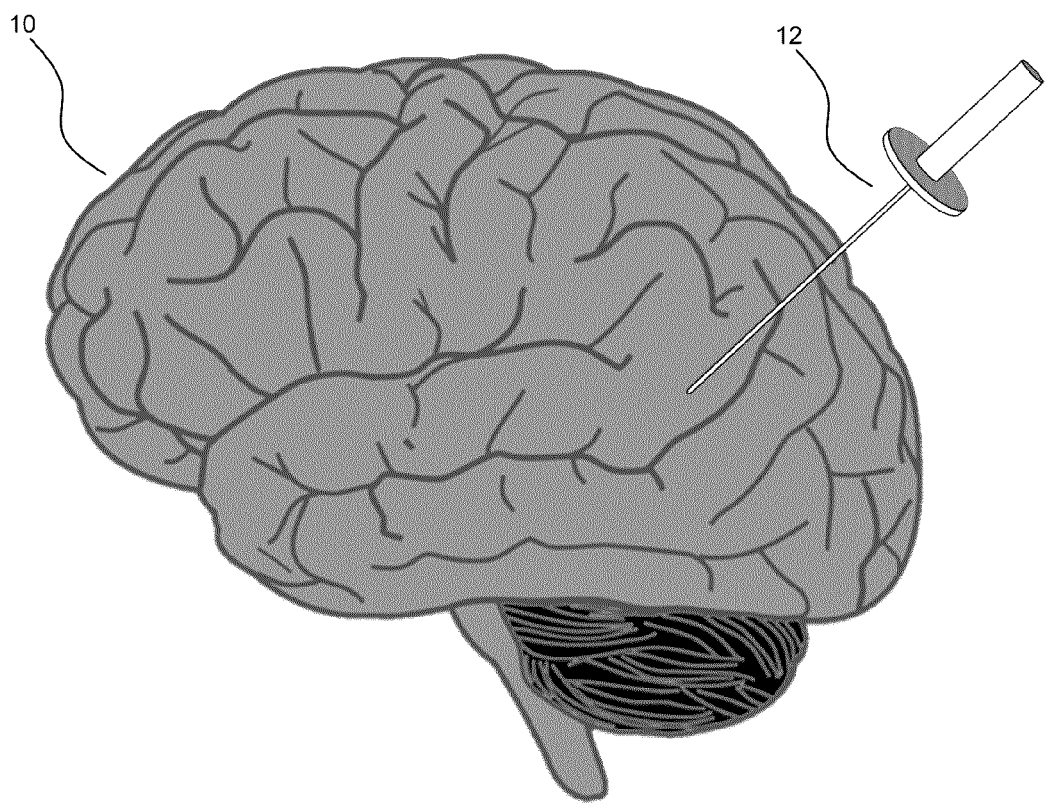
FIG. 1 illustrates the insertion of an access port into a human brain, for providing access to internal brain tissue during a medical procedure.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. In one non-limiting example, the terms "about" and "approximately" mean plus or minus 10 percent or less.

Unless defined otherwise, all technical and scientific terms used herein are intended to have the same meaning as commonly understood by one of ordinary skill in the art. Unless otherwise indicated, such as through context, as used herein, the following terms are intended to have the following meanings:

As used herein, the phrase "access port" refers to a cannula, conduit, sheath, port, tube, or other structure that is insertable into a subject, in order to provide access to internal tissue, organs, or other biological substances. In some embodiments, an access port may directly expose internal tissue, for example, via an opening or aperture at a distal end thereof, and/or via an opening or aperture at an intermediate location along a length thereof. In other embodiments, an access port may provide indirect access, via one or more surfaces that are transparent, or partially transparent, to one or more forms of energy or radiation, such as, but not limited to, electromagnetic waves and acoustic waves.

As used herein the phrase "intraoperative" refers to an action, process, method, event or step that occurs or is carried out during at least a portion of a medical procedure. Intraoperative, as defined herein, is not limited to surgical procedures, and may refer to other types of medical procedures, such as diagnostic and therapeutic procedures.

Embodiments of the present disclosure provide imaging devices that are insertable into a subject or patient for imaging internal tissues, and methods of use thereof. Some embodiments of the present disclosure relate to minimally invasive medical procedures that are performed via an access port, whereby surgery, diagnostic imaging, therapy, or other medical procedures (e.g. minimally invasive medical procedures) are performed based on access to internal tissue through the access port.

Figure 2:
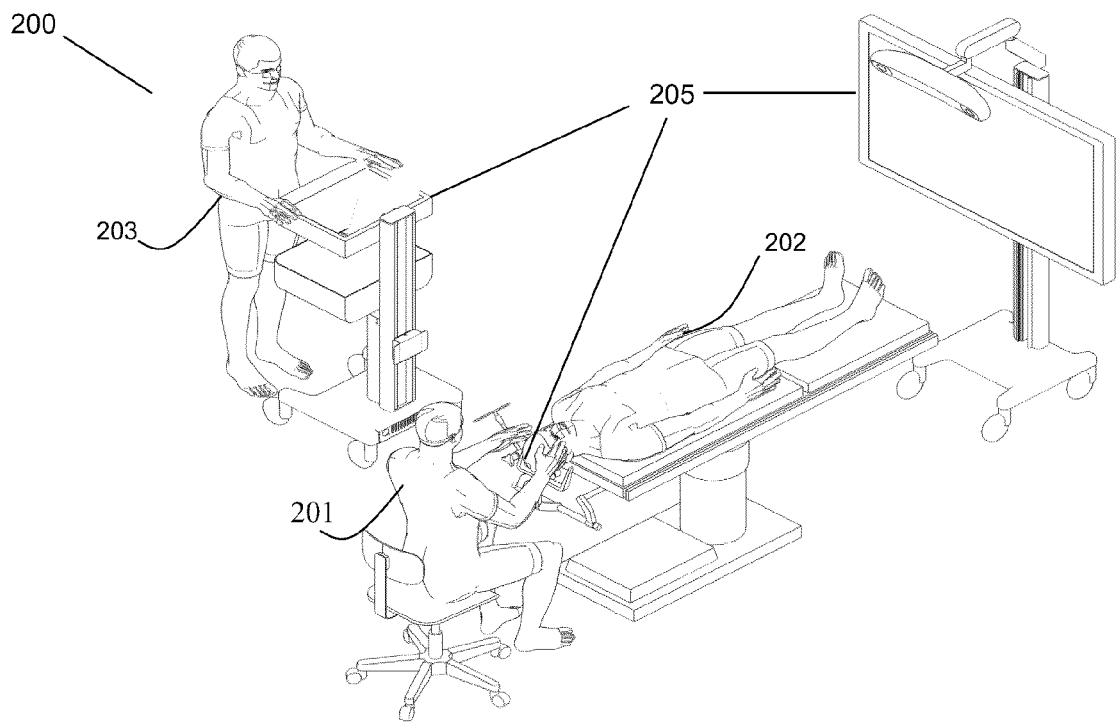
FIG. 2 shows an exemplary navigation system to support minimally invasive access port-based surgery.

Referring to FIG. 2, an exemplary navigation system environment 200 is shown, which may be used to support navigated image-guided surgery. As shown in FIG. 2, surgeon 201 conducts a surgery on a patient 202 in an operating room (OR) environment. A medical navigation system 205 comprising an equipment tower, tracking system, displays and tracked instruments assist the surgeon 201 during his procedure. An operator 203 is also present to operate, control and provide assistance for the medical navigation system 205.

Figure 3:
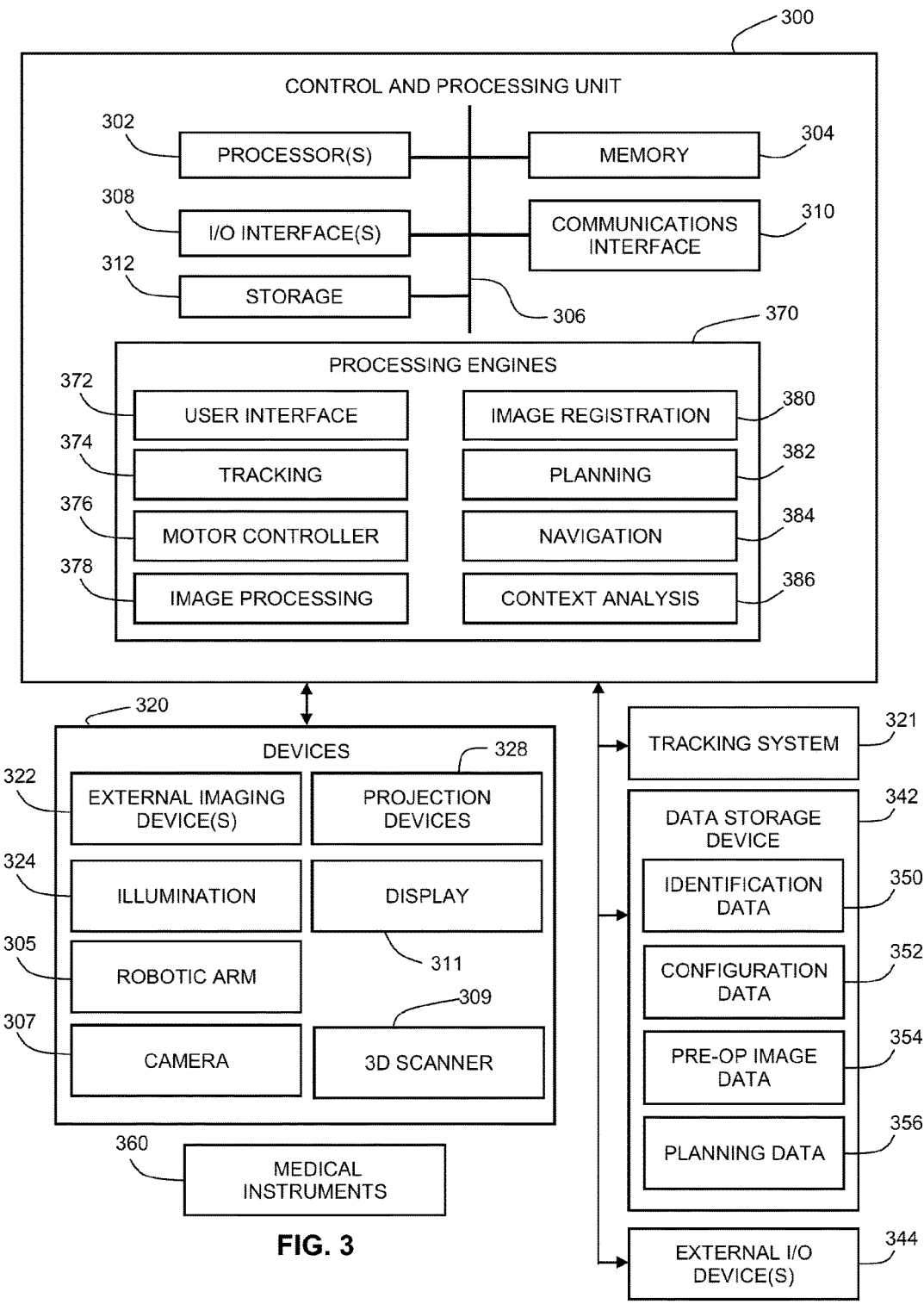
FIG. 3 is a block diagram illustrating a control and processing system that may be used in the navigation system shown in FIG. 2.

Referring to FIG. 3, a block diagram is shown illustrating a control and processing system 300 that may be used in the medical navigation system 200 shown in FIG. 3 (e.g., as part of the equipment tower). As shown in FIG. 3, in one example, control and processing system 300 may include one or more processors 302, a memory 304, a system bus 306, one or more input/output interfaces 308, a communications interface 310, and storage device 312. Control and processing system 300 may be interfaced with other external devices, such as tracking system 321, data storage 342, and external user input and output devices 344, which may include, for example, one or more of a display, keyboard, mouse, sensors attached to medical equipment, foot pedal, and microphone and speaker. Data storage 342 may be any suitable data storage device, such as a local or remote computing device (e.g. a computer, hard drive, digital media device, or server) having a database stored thereon. In the example shown in FIG. 3, data storage device 342 includes identification data 350 for identifying one or more medical instruments 360 and configuration data 352 that associates customized configuration parameters with one or more medical instruments 360. Data storage device 342 may also include preoperative image data 354 and/or medical procedure planning data 356. Although data storage device 342 is shown as a single device in FIG. 3, it will be understood that in other embodiments, data storage device 342 may be provided as multiple storage devices.

Medical instruments 360 are identifiable by control and processing unit 300. Medical instruments 360 may be connected to and controlled by control and processing unit 300, or medical instruments 360 may be operated or otherwise employed independent of control and processing unit 300. Tracking system 321 may be employed to track one or more of medical instruments 360 and spatially register the one or more tracked medical instruments to an intraoperative reference frame. For example, medical instruments 360 may include tracking spheres that may be recognizable by a tracking camera 307. In one example, the tracking camera 307 may be an infrared (IR) tracking camera. In another example, as sheath placed over a medical instrument 360 may be connected to and controlled by control and processing unit 300.

Control and processing unit 300 may also interface with a number of configurable devices, and may intraoperatively reconfigure one or more of such devices based on configuration parameters obtained from configuration data 352. Examples of devices 320, as shown in FIG. 3, include one or more external imaging devices 322, one or more illumination devices 324, a robotic arm 305, one or more projection devices 328, a display 211, and a 3D scanner 309.

Exemplary aspects of the disclosure can be implemented via processor(s) 302 and/or memory 304. For example, the functionalities described herein can be partially implemented via hardware logic in processor 302 and partially using the instructions stored in memory 304, as one or more processing modules or engines 370. Example processing modules include, but are not limited to, user interface engine 372, tracking module 374, motor controller 376, image processing engine 378, image registration engine 380, procedure planning engine 382, navigation engine 384, and context analysis module 386. While the example processing modules are shown separately in FIG. 3, in one example the processing modules 370 may be stored in the memory 304 and the processing modules may be collectively referred to as processing modules 370.

It is to be understood that the system is not intended to be limited to the components shown in FIG. 3. One or more components of the control and processing system 300 may be provided as an external component or device. In one example, navigation module 384 may be provided as an external navigation system that is integrated with control and processing system 300.

Some embodiments may be implemented using processor 302 without additional instructions stored in memory 304. Some embodiments may be implemented using the instructions stored in memory 304 for execution by one or more general purpose microprocessors. Thus, the disclosure is not limited to a specific configuration of hardware and/or software.

While some embodiments can be implemented in fully functioning computers and computer systems, various embodiments are capable of being distributed as a computing product in a variety of forms and are capable of being applied regardless of the particular type of machine or computer readable media used to actually effect the distribution.

At least some aspects disclosed can be embodied, at least in part, in software. That is, the techniques may be carried out in a computer system or other data processing system in response to its processor, such as a microprocessor, executing sequences of instructions contained in a memory, such as ROM, volatile RAM, non-volatile memory, cache or a remote storage device.

A computer readable storage medium can be used to store software and data which, when executed by a data processing system, causes the system to perform various methods. The executable software and data may be stored in various places including for example ROM, volatile RAM, nonvolatile memory and/or cache. Portions of this software and/or data may be stored in any one of these storage devices.

Examples of computer-readable storage media include, but are not limited to, recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions may be embodied in digital and analog communication links for electrical, optical, acoustical or other forms of propagated signals, such as carrier waves, infrared signals, digital signals, and the like. The storage medium may be the internet cloud, or a computer readable storage medium such as a disc.

At least some of the methods described herein are capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, USB keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

According to one aspect of the present application, one purpose of the navigation system 205, which may include control and processing unit 300, is to provide tools to the neurosurgeon that will lead to the most informed, least damaging neurosurgical operations. In addition to removal of brain tumours and intracranial hemorrhages (ICH), the navigation system 205 can also be applied to a brain biopsy, a functional/deep-brain stimulation, a catheter/shunt placement procedure, open craniotomies, endonasal/skull-based/ENT, spine procedures, and other parts of the body such as breast biopsies, liver biopsies, etc. While several examples have been provided, aspects of the present disclosure may be applied to any suitable medical procedure.

Figure 4A:
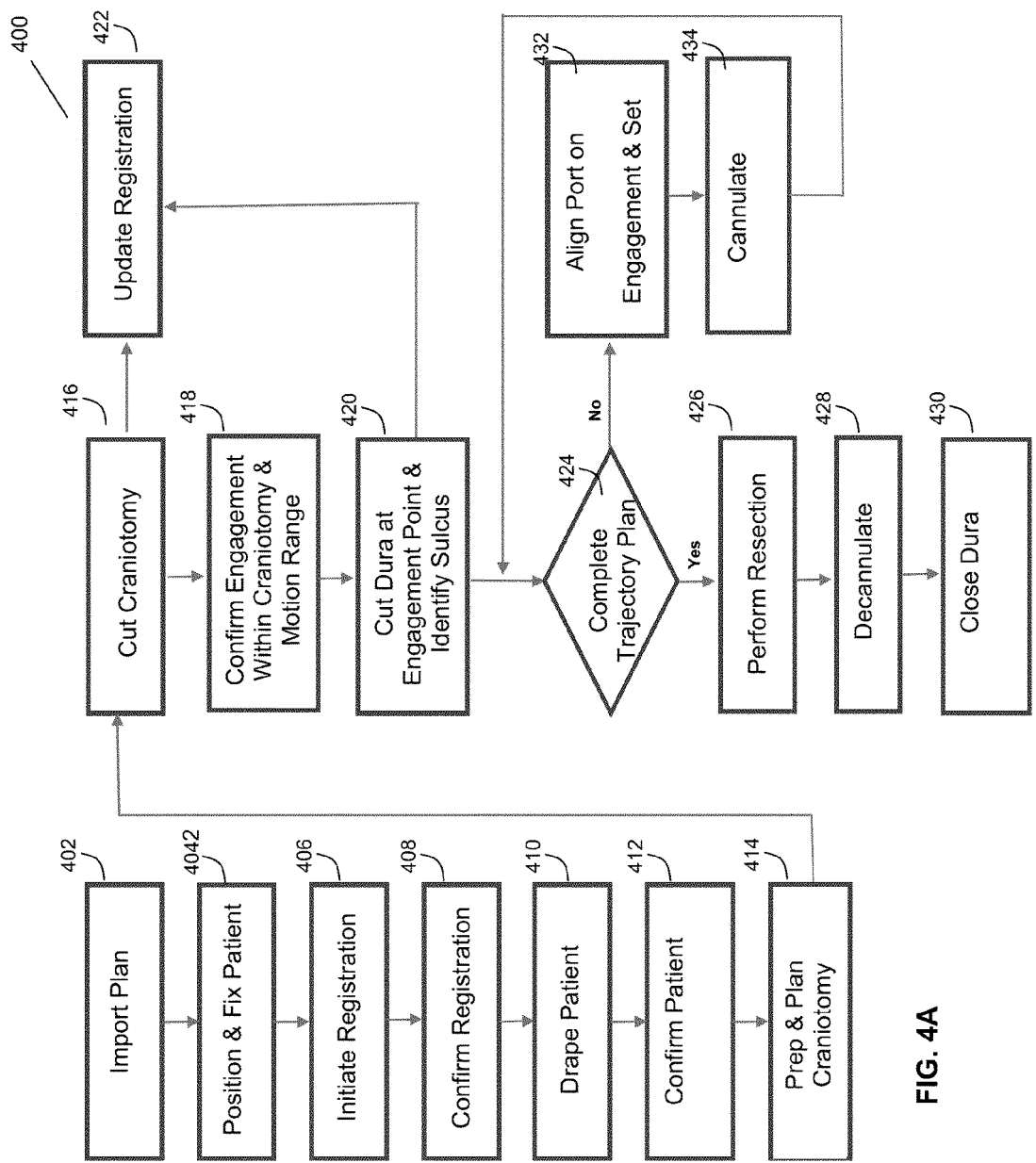
FIG. 4A is a flow chart illustrating a method involved in a surgical procedure using the navigation system of FIG. 2.

Referring to FIG. 4A, a flow chart is shown illustrating a method 400 of performing a port-based surgical procedure using a navigation system, such as the medical navigation system 200 described in relation to FIG. 2. At a first block 402, the port-based surgical plan is imported. A detailed description of the process to create and select a surgical plan is outlined in international publication WO/2014/139024, entitled "PLANNING, NAVIGATION AND SIMULATION SYSTEMS AND METHODS FOR MINIMALLY INVASIVE THERAPY", which claims priority to U.S. Provisional Patent Application Ser. Nos. 61/800,155 and 61/924,993, which are all hereby incorporated by reference in their entirety.

Once the plan has been imported into the navigation system at the block 402, the patient is affixed into position using a body holding mechanism. The head position is also confirmed with the patient plan in the navigation system (block 404), which in one example may be implemented by the computer or controller forming part of the equipment tower of medical navigation system 205.

Next, registration of the patient is initiated (block 406). The phrase "registration" or "image registration" refers to the process of transforming different sets of data into one coordinate system. Data may includes multiple photographs, data from different sensors, times, depths, or viewpoints. The process of "registration" is used in the present application for medical imaging in which images from different imaging modalities are co-registered. Registration is used in order to be able to compare or integrate the data obtained from these different modalities.

Those skilled in the relevant arts will appreciate that there are numerous registration techniques available and one or more of the techniques may be applied to the present example. Non-limiting examples include intensity-based methods that compare intensity patterns in images via correlation metrics, while feature-based methods find correspondence between image features such as points, lines, and contours. Image registration methods may also be classified according to the transformation models they use to relate the target image space to the reference image space. Another classification can be made between single-modality and multi-modality methods. Single-modality methods typically register images in the same modality acquired by the same scanner or sensor type, for example, a series of magnetic resonance (MR) images may be co-registered, while multi-modality registration methods are used to register images acquired by different scanner or sensor types, for example in magnetic resonance imaging (MRI) and positron emission tomography (PET). In the present disclosure, multi-modality registration methods may be used in medical imaging of the head and/or brain as images of a subject are frequently obtained from different scanners. Examples include registration of brain computerized tomography (CT)/MRI images or PET/CT images for tumor localization, registration of contrast-enhanced CT images against non-contrast-enhanced CT images, and registration of ultrasound and CT.

Figure 4B:
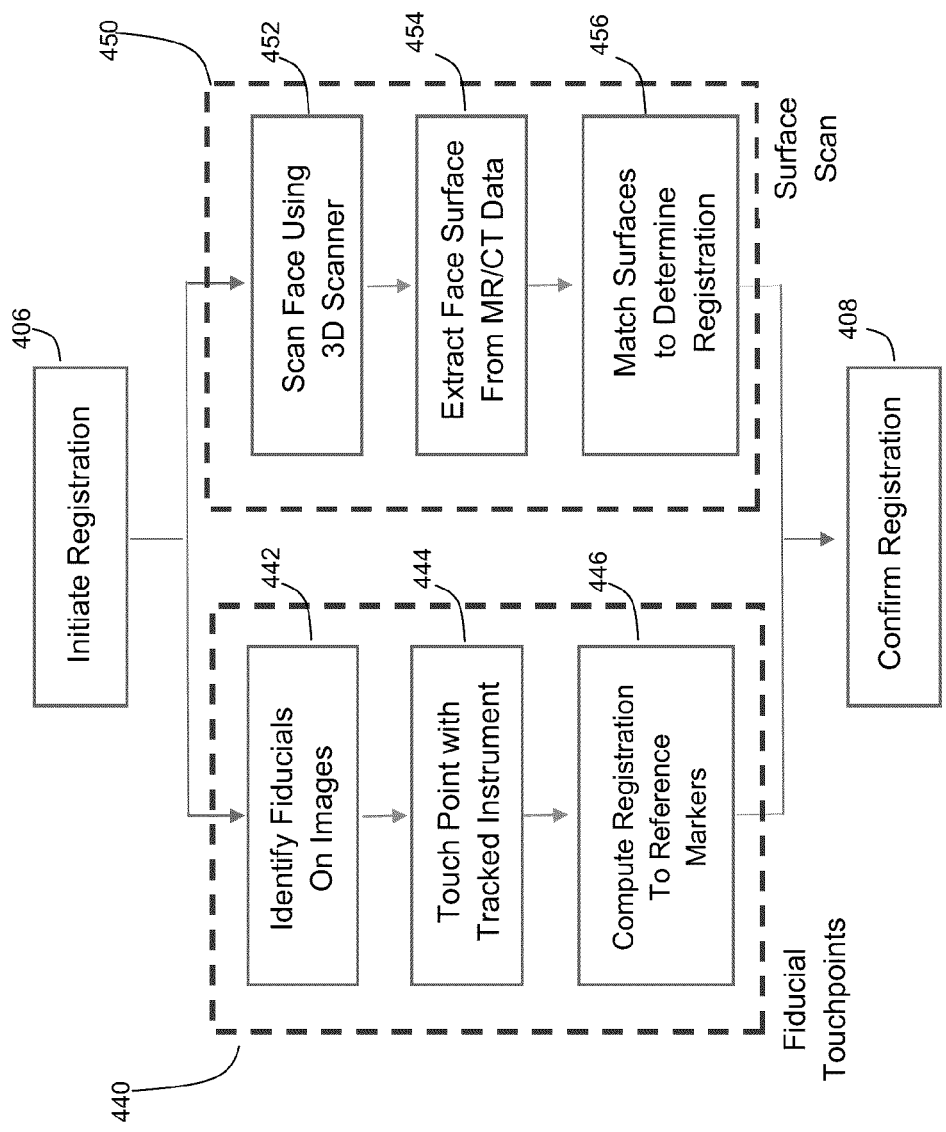
FIG. 4B is a flow chart illustrating a method of registering a patient for a surgical procedure as outlined in FIG. 4A.

Referring now to FIG. 4B, a flow chart is shown illustrating a method involved in registration block 406 as outlined in FIG. 4A, in greater detail. If the use of fiducial touch points (440) is contemplated, the method involves first identifying fiducials on images (block 442), then touching the touch points with a tracked instrument (block 444). Next, the navigation system computes the registration to reference markers (block 446).

Alternately, registration can also be completed by conducting a surface scan procedure (block 450). The block 450 is presented to show an alternative approach, but may not typically be used when using a fiducial pointer. First, the face is scanned using a 3D scanner (block 452). Next, the face surface is extracted from MR/CT data (block 454). Finally, surfaces are matched to determine registration data points (block 456).

Upon completion of either the fiducial touch points (440) or surface scan (450) procedures, the data extracted is computed and used to confirm registration at block 408, shown in FIG. 4A.

Referring back to FIG. 4A, once registration is confirmed (block 408), the patient is draped (block 410). Typically, draping involves covering the patient and surrounding areas with a sterile barrier to create and maintain a sterile field during the surgical procedure. The purpose of draping is to eliminate the passage of microorganisms (e.g., bacteria) between non-sterile and sterile areas. At this point, conventional navigation systems require that the non-sterile patient reference is replaced with a sterile patient reference of identical geometry location and orientation. Numerous mechanical methods may be used to minimize the displacement of the new sterile patient reference relative to the non-sterile one that was used for registration but it is inevitable that some error will exist. This error directly translates into registration error between the surgical field and pre-surgical images. In fact, the further away points of interest are from the patient reference, the worse the error will be.

Upon completion of draping (block 410), the patient engagement points are confirmed (block 412) and then the craniotomy is prepared and planned (block 414).

Upon completion of the preparation and planning of the craniotomy (block 414), the craniotomy is cut and a bone flap is temporarily removed from the skull to access the brain (block 416). Registration data is updated with the navigation system at this point (block 422).

Next, the engagement within craniotomy and the motion range are confirmed (block 418). Next, the procedure advances to cutting the dura at the engagement points and identifying the sulcus (block 420).

Thereafter, the cannulation process is initiated (block 424). Cannulation involves inserting a port into the brain, typically along a sulci path as identified at 420, along a trajectory plan. Cannulation is typically an iterative process that involves repeating the steps of aligning the port on engagement and setting the planned trajectory (block 432) and then cannulating to the target depth (block 434) until the complete trajectory plan is executed (block 424).

Once cannulation is complete, the surgeon then performs resection (block 426) to remove part of the brain and/or tumor of interest. The surgeon then decannulates (block 428) by removing the port and any tracking instruments from the brain. Finally, the surgeon closes the dura and completes the craniotomy (block 430). Some aspects of FIG. 4A are specific to port-based surgery, such portions of blocks 428, 420, and 434, but the appropriate portions of these blocks may be skipped or suitably modified when performing non-port based surgery.

When performing a surgical procedure using a medical navigation system 205, as outlined in connection with FIGS. 4A and 4B, the medical navigation system 205 must acquire and maintain a reference of the location of the tools in use as well as the patient in three dimensional (3D) space. In other words, during a navigated neurosurgery, there needs to be a tracked reference frame that is fixed relative to the patient's skull. During the registration phase of a navigated neurosurgery (e.g., the step 406 shown in FIGS. 4A and 4B), a transformation is calculated that maps the frame of reference of preoperative MRI or CT imagery to the physical space of the surgery, specifically the patient's head. This may be accomplished by the navigation system 205 tracking locations of fiducial markers fixed to the patient's head, relative to the static patient reference frame. The patient reference frame is typically rigidly attached to the head fixation device, such as a Mayfield clamp. Registration is typically performed before the sterile field has been established (e.g., the step 410 shown in FIG. 4A).

Most conventional navigation systems require the patient reference be exchanged during the draping phase (e.g., step 410) and the original patient reference frame used for registration is replaced with a sterile patient reference frame. This exchange can cause a loss of accuracy.

Other conventional systems may require the non-sterile reference frame to be draped with a sterile, transparent plastic surgical drape. Where tracking spheres are used in conjunction with an infrared (IR) tracking camera, visibility through this drape can cause optical distortion of the measured reference position and can cause loss of accuracy. This process is also operator and set-up dependent, being affected by how the sterile drape is positioned and how tightly it is formed around the reference frame.

Also, throughout a navigated surgery, the patient reference frame is sometimes bumped by the surgeon or others involved into the procedure. A bump that is strong enough could cause a shift in the frame's location and therefore create a misregistration.

In order to address the shortcomings of conventional systems outlined above, according to one aspect of the present description, a patient reference design is provided that incorporates a removable sterile cover. According to another aspect of the present description, a sensor may be attached to or embedded in the patient reference frame to provide the medical navigation system 205 with information that can be used to determine when the patient reference frame is bumped with enough force that the frame's location may have to be re-registered.

The sterile drape may include a plastic lens that is placed over the patient reference face containing the tracking markers. In one example, the sterile cover maybe a substantially rigid lens. In one example, the markers could be active IR markers or passive reflective spheres. The sterile cover may not cause significant distortion like a standard drape would. The sterile cover may have a transparent plastic sock that extends downward from the cover to cover the rest of the patient reference and patient reference mounting arm and extension. The patient reference may be designed to permit +/−45 degree line-of-sight between the tracking camera 307 (e.g., a Northern Digital Polaris Spectra) and the patient reference.

Force Sensors and/or accelerometers may be connected to the medical navigation system 205, either wired or wirelessly, and the medical navigation system 205 may display a warning and/or force re-registration if too great of a force and/or acceleration is imparted on the patient reference.

Figure 5:
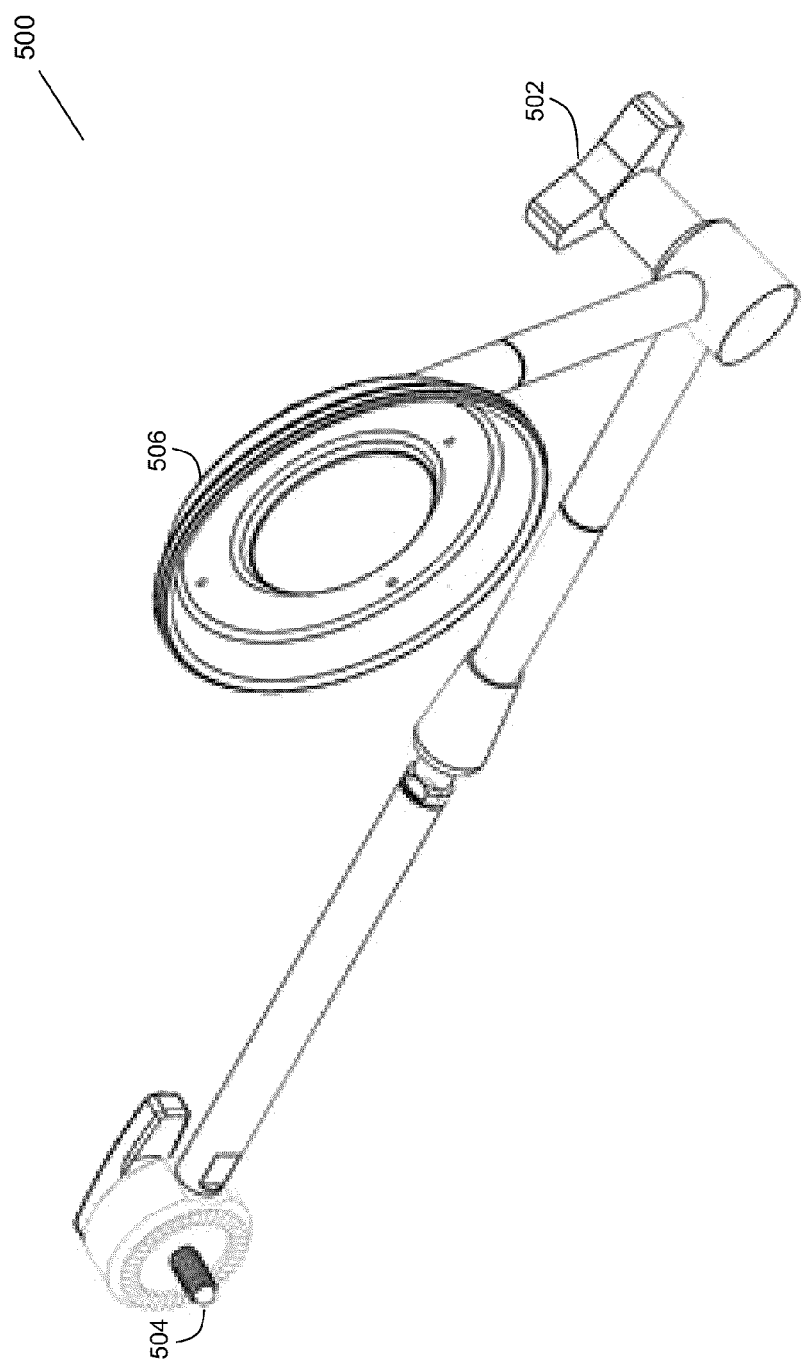
FIG. 5 is a perspective drawing illustrating an exemplary arm for holding a patient reference device.

Referring to FIG. 5, an exemplary arm 500 is shown for holding a patient reference device. Arm 500 may also be referred to a patient reference arm 500. Patient reference arm 500 may include a tightening screw 502 for securing the patient reference arm 500 once patient reference arm 500 has been suitably adjusted. Patient reference arm 500 may attach to a Mayfield head holder or other suitable head holding device using mounting bolt 504. In another example, patient reference arm 500 may attach directly to a patient bed so long as the spatial relationship between the receiving device for mounting bolt 504 and the patient's head is static and known by medical navigation system 205. The mounting bolt 504 may secure the patient reference arm 500 to a Mayfield clamp. Once the tightening screw 502 is tightened the arm 500 may not pivot; the user may clock the arm 500 to his desired position using the starbust connection. Once the screw 502 is tightened, a rigid connection between the Mayfield clamp and the arm 500 is provided. While one example of an arm 500 for connecting a patient reference device with a head holding device has been shown, any suitable arm or connecting mechanism may be used according to the design criteria of a particular application.

Figure 6B:
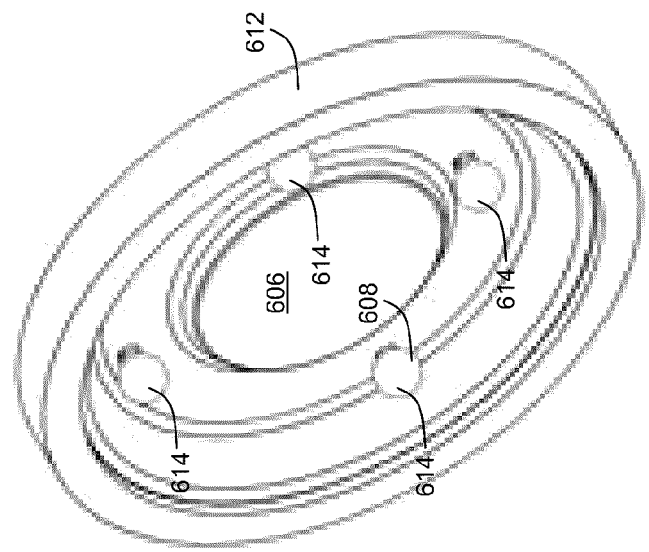
FIG. 6B is a perspective drawing illustrating an exemplary patient reference device with cover attached.
Figure 6A:
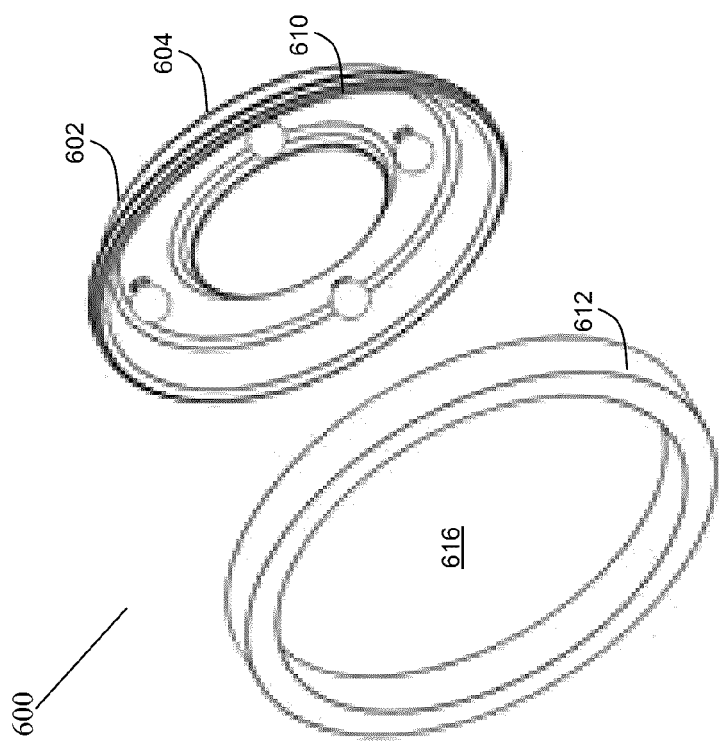
FIG. 6A is a perspective drawing illustrating an exemplary patient reference device with cover detached.
Figure 7:
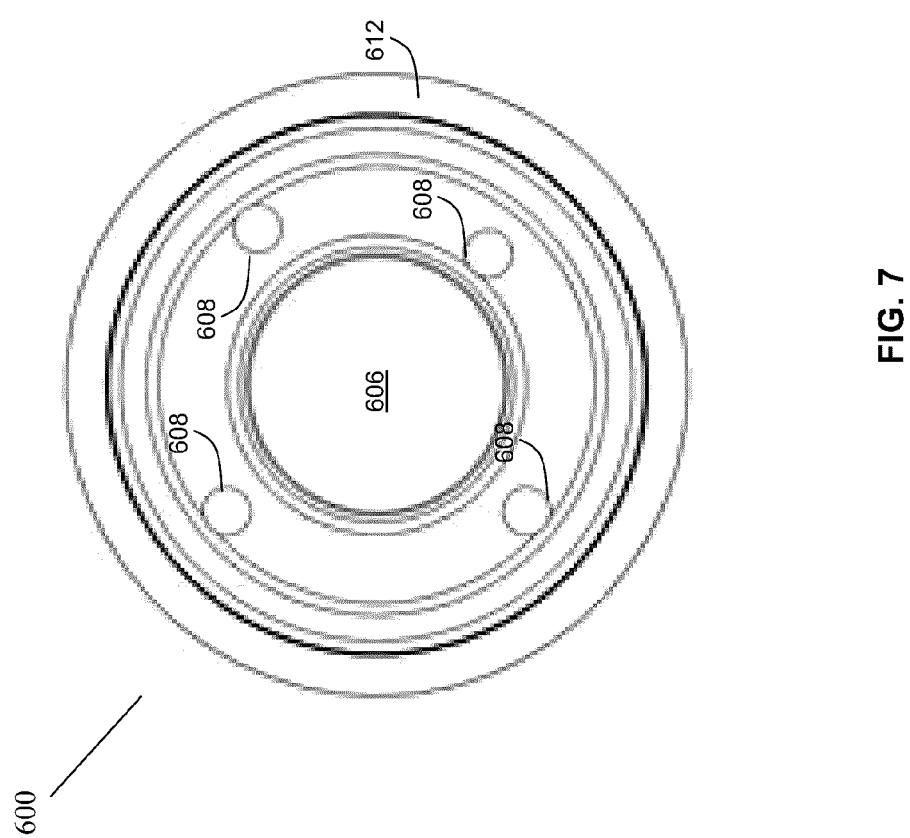
FIG. 7 is a front view of the exemplary patient reference device shown in FIG. 6B.
Figure 8:
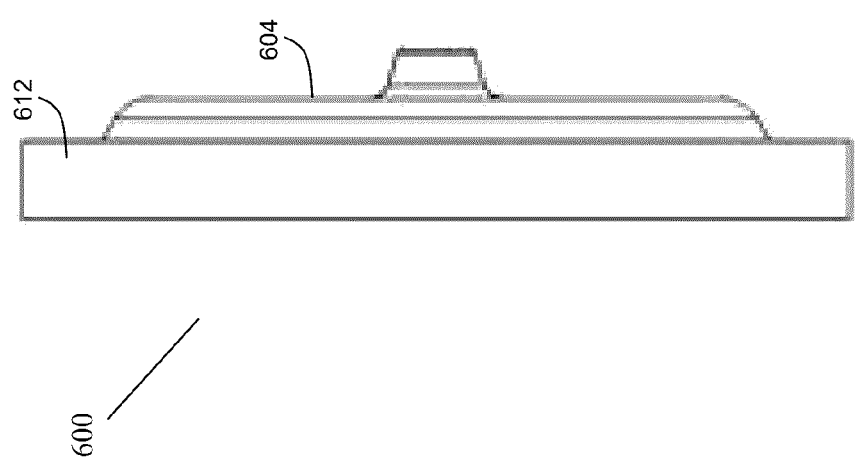
FIG. 8 is a side view of the exemplary patient reference device shown in FIG. 6B.

Referring to FIGS. 6A and 6B, an exemplary patient reference device 600 is shown according to one aspect of the present application. FIG. 6a shows a perspective drawing illustrating the patient reference device 600 with a cover detached. FIG. 6b shows a perspective drawing of the patient reference device 600 with the cover attached. FIG. 7 shows a front view of the patient reference device with the drape attached. FIG. 8 shows a side view of the patient reference device 600 with the drape attached. FIGS. 6-8 are now discussed concurrently.

The patient reference device 600 may be used during a medical procedure. The patient reference device 600 includes a housing 602 having a back side 604 and a front side 606. In one example, at least three tracking markers 608 are attached to the front side 606 of the housing 602. In another example, four or more tracking makers 608 may be used. The tracking markers 608 each have a top 614, generally on the opposite side from where the tracking markers 608 attach to the housing 602. While an example of either three or four tracking markers 608 is provided, any number of tracking markers 608 may be used to meet the design criteria of a particular application. In one example, only one or two tracking markers may be used. In one example, the tracking markers 608 may be passive reflective tracking spheres or active infrared (IR) markers that may be visible to a tracking camera, such as the tracking camera 307 of the medical navigation system 205. In another example, the tracking markers 608 may be active light emitting diodes (LEDs) or a graphical pattern printed on a three dimensional (3D) structure used by a vision system such as the tracking camera to acquire 6 degrees of freedom (DOF).

The housing 602 shown in FIG. 6 is generally disc shaped. However, any suitable shaped housing or frame may be used to meet the design criteria of a particular application. In some examples, the housing 602 may be a solid member, either square shaped or disc shaped and the frame may further have superfluous material removed that is not important to the structural integrity of the housing (e.g., the housing may be generally square shaped or disc shaped with holes formed therein). In one example, the housing 602 may be constructed of a metal such as machined aluminum, blasted with aluminum oxide (e.g., 180 grit), and then hard anodized. Both the blasting and anodization processes may result in a matte finish of the housing 602 that may minimize reflection seen by the tracking camera. Naked metallic surfaces or even plastic sometimes lead to poor accuracy for camera based tracking systems due to the presence of reflection, which can be further magnified with the use of a plastic drape on the patient reference 600. The exemplary blasted and anodized aluminum finish may improve tracking performance of the tracking camera without degrading accuracy. While one example of a suitable finish for the housing 602 is provided, any suitable finish of low reflectivity may be used to meet the design criteria of a particular application. In one example, the housing 602 may be made of any suitable type of plastic or metal.

The housing 602 shown in FIGS. 6-8 extends along the back side 604 of the housing 602. The housing 602 further extends beyond a horizontal plane defined by the tops 614 of the tracking markers 608. The housing terminates at an edge 610. In one example, the edge 610 may be substantially continuous, such as forming a shape such as a circle, a square, an oval, or a rectangle in one plane. A sterile cover 612 may be attached to the substantially continuous edge 610 of the housing 602 for covering the housing 602 and the tracking markers 608. In one example, the housing 602 may be generally domed shaped with a flattened back side and the sterile cover 612 may be round. However, the housing 602 may also be pyramid shaped, cone shaped, dome shaped, dish shaped, or of any other suitable shape to meet the design criteria of a particular application. The shape of the sterile cover 612 is then designed to mate appropriately with the shape of the housing 602.

The housing 602 of the patient reference device 600 may be attachable to a patient reference arm, such as the patient reference arm 500 shown in FIG. 5. The patient reference arm 500 may be attachable by way of the mounting bolt 510 to a Mayfield head holder or any other head securing device, such that the patient reference device 600 is rigidly attached in a static location relative to the head securing device.

In one example, the continuous edge 610 may have a seal located on the continuous edge 610 for forming a seal between the housing 602 and the sterile cover 612. In one example, the seal may be attached to the continuous edge 610 using any suitable adhesive. The sterile cover 612 may further have a sterile drape attached thereto for covering the housing 602 and a patient reference arm 500 attached to and holding the patient reference device 600 in position.

In one example, a lens 616 of the sterile cover 612 may be made of a substantially transparent plastic material that can be easily sterilized and has optical properties that are known and controlled such that infrared light passing through the lens 616 of the sterile cover 612 and reflecting off of the tracking markers 608 and passing back through the lens 616 of sterile cover 612 does so without excessive diffraction such that it becomes problematic for the tracking camera (e.g., the tracking camera 307) that is monitoring the tracking markers 608. In one example, the sterile cover 612 could be made of glass, quartz, or sapphire. In some examples, the lens 616 of the sterile cover 612 may have additional optical properties, such as that of a band pass filter that allows infrared light to pass through but blocks any suitable portion of the frequency spectrum on each side of the IR pass band. In another example, the lens 616 of the sterile cover 612 may have the optical properties of a low pass or a high pass optical filter. Alternatively, the optical properties of the lens 616 of the sterile cover 612 may be optimized for passing visible light or only visible light in the example where a graphical pattern is printed on a structure. While some examples have been given for possible optical filter characteristics, any suitable optical filter may be applied to the lens 616 to meet the design criteria of a particular application.

The patient reference device 600 may further have one or more sensors (not shown) attached thereto for providing a signal to a medical navigation system, such as the medical navigation system 205 shown in FIG. 2, which may include the control and processing unit 300 shown in FIG. 3. In one example, the sensor may include, an accelerometer, a force sensor, a gyroscope, a magnetometer, a strain gauge, or any other suitable sensor. The sensor may be either attached to the exterior of the housing 602 or embedded in or integrated into the housing 602. In one example, the patient reference device 600 may have a triaxial accelerometer attached thereto for sensing acceleration in any of the X, Y, and Z directions and providing the signal generated by the accelerometer to the control and processing unit 300. For example, the accelerometer mounted on the patient reference device 600 may be shown in FIG. 3 as one of the external I/O devices 344. The control and processing unit 300 may be programmed (e.g., one of the processing engines 370) to monitor signals from the accelerometer after the patient reference device 600 has been put into position and registered during the registrations phases 406/408 (FIG. 4A).

When the control and processing system 300 detects an acceleration from the accelerometer that indicates that the patient reference device 600 or the patient reference arm 500 has been jolted, perhaps by one of the medical staff accidentally hitting or kicking the patient reference device 600 or the patient reference arm 500, and when the acceleration indicated by the accelerometer exceeds a threshold such that enough force was generated that could have thrown the patient reference device out of its proper fixed position, the control and processing system 300 may respond accordingly. For example, the control and processing system 300 may display a warning on the display 311 to the operator to check the position of the patient reference device 600. In another example, the control and processing system 300 may simply require the operator of the system to reregister the patient reference device 600 to ensure that the position of the patient reference device 600 relative to the head holding device is properly understood by the medical navigation system 205.

Referring now to FIG. 9A, a perspective drawing is shown illustrating an environmental context of the exemplary patient reference device 600 shown in FIG. 6. In FIG. 9A, the patient reference device 600 is shown attached to an arm that fixes the patient reference device 600 in position at the head end of a medical bed for performing a medical procedure in an operating room type environment, as discussed above. Several aspects of the navigation system 205 discussed in connection with FIG. 2 are shown surrounding the medical bed.

Figure 9B:
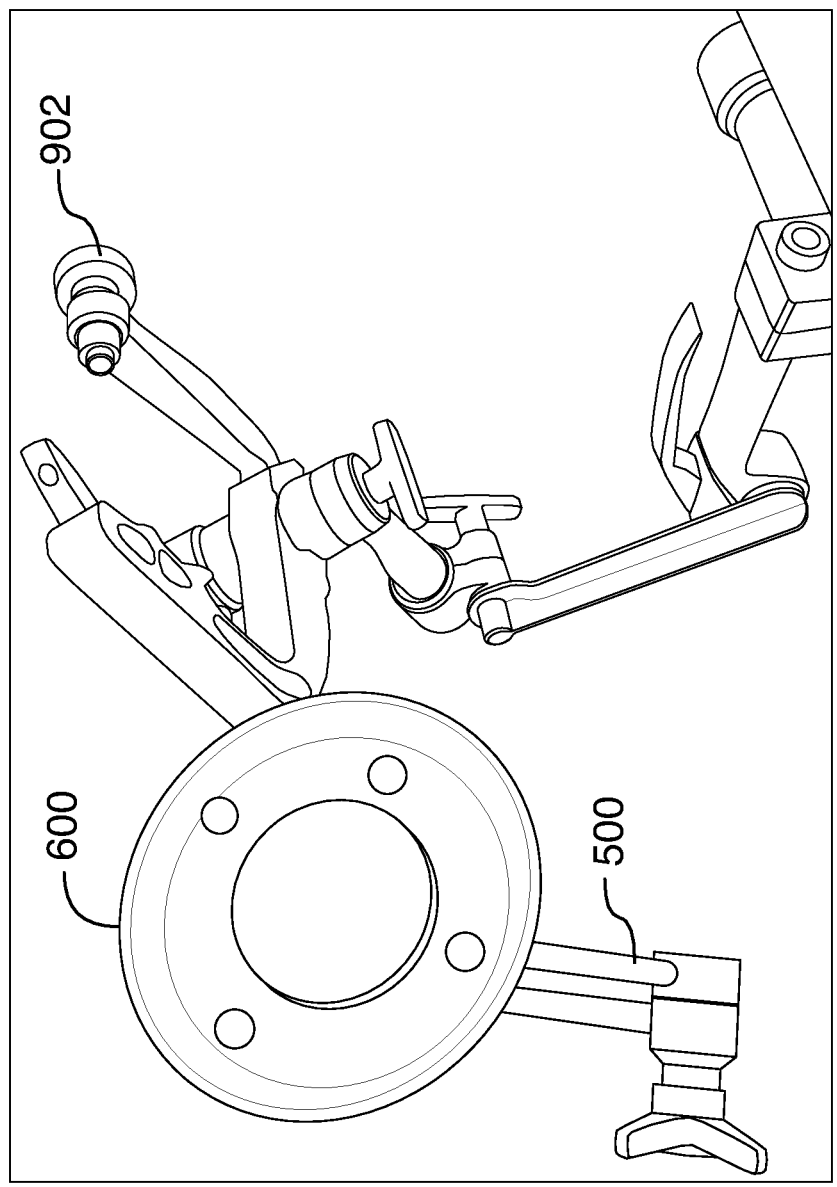
FIG. 9B is a perspective drawing showing the exemplary patient reference device shown in FIG. 6 installed.
Figure 9C:
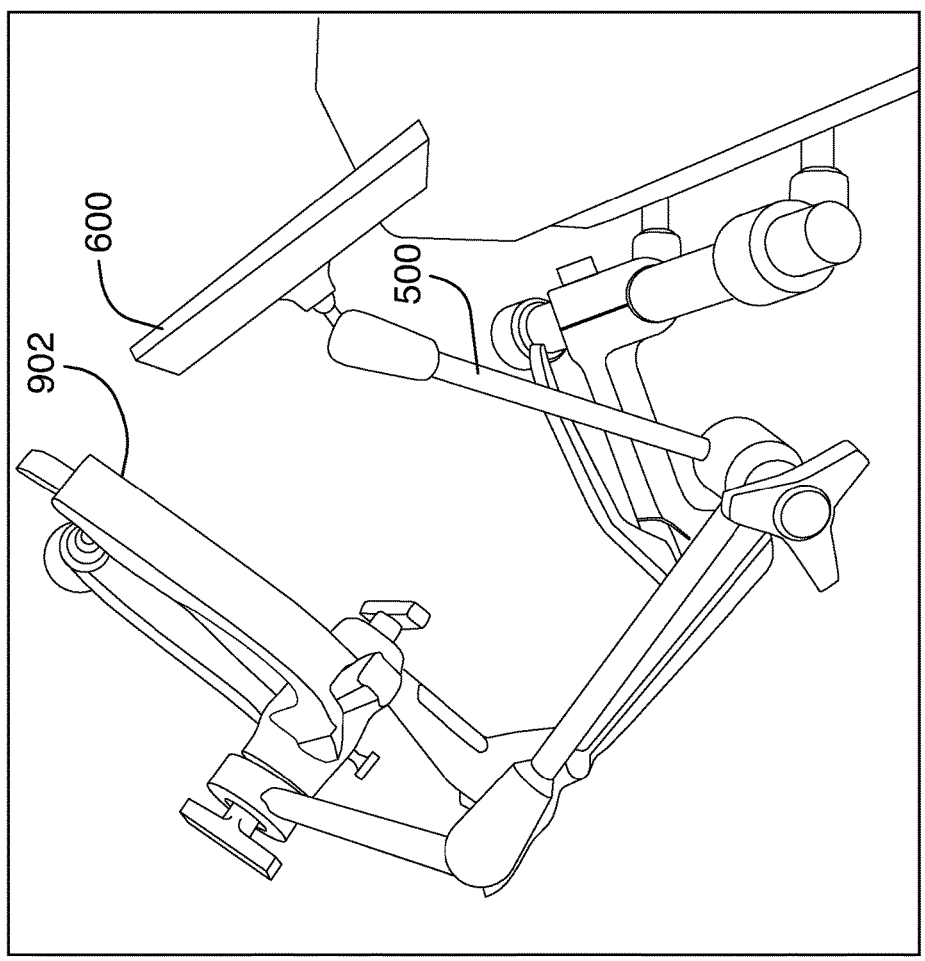
FIG. 9C is a perspective drawing showing the exemplary patient reference device shown in FIG. 6 installed.
Figure 9D:
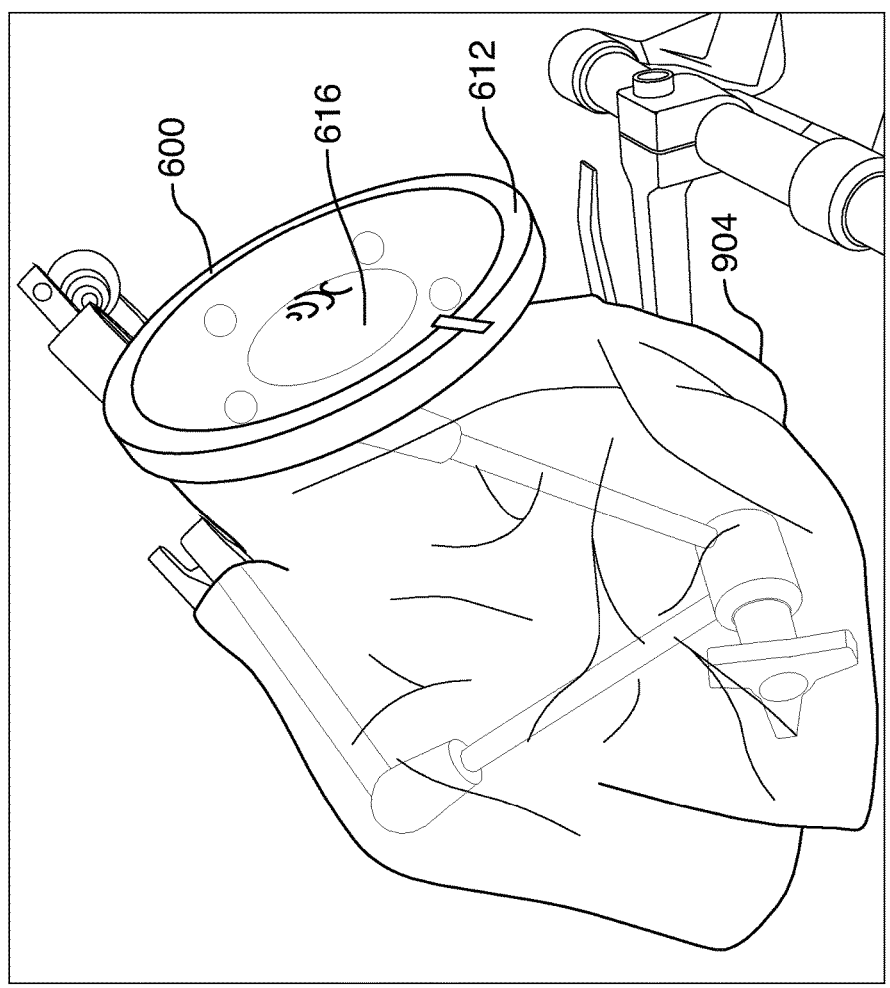
FIG. 9D is a perspective drawing showing the exemplary patient reference device shown in FIG. 6 installed with sterile draping in place.
Figure 9E:
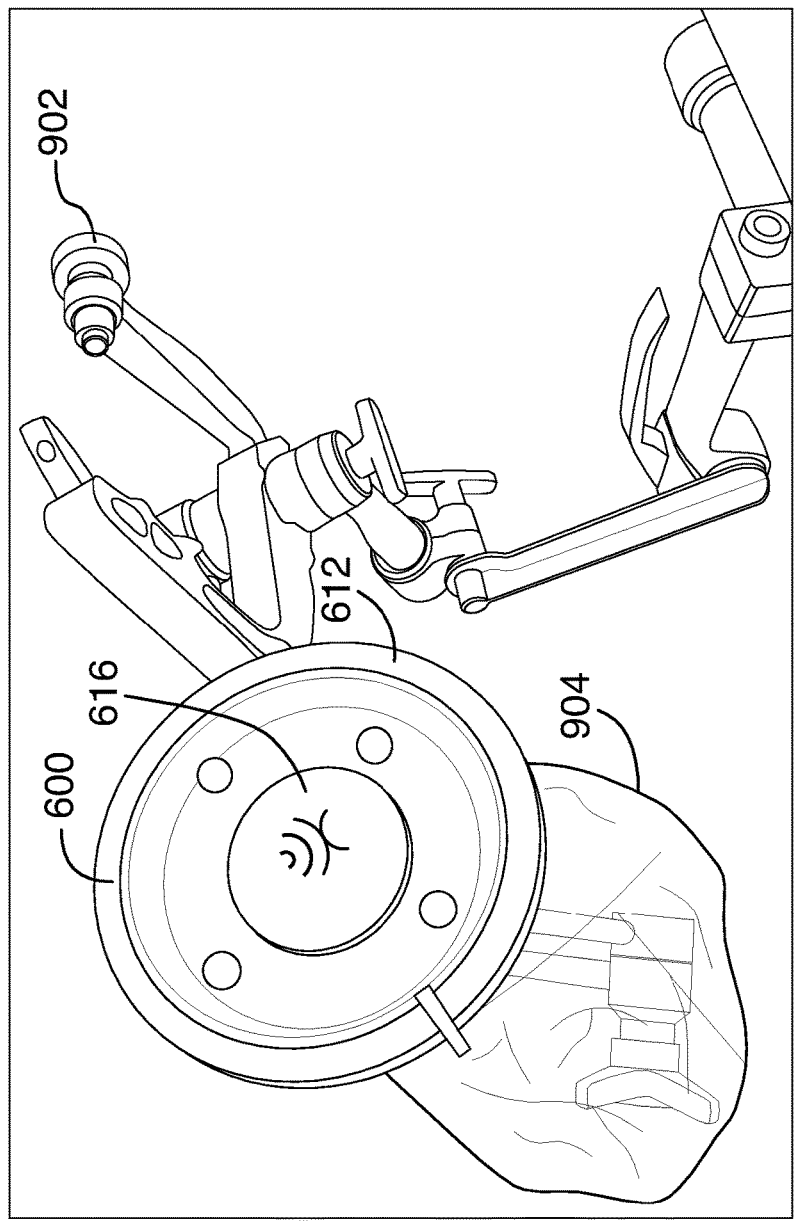
FIG. 9E is a perspective drawing showing the exemplary patient reference device shown in FIG. 6 installed with sterile draping in place.

Referring now to FIG. 9B, a perspective drawing is shown illustrating the exemplary patient reference device 600 installed. FIG. 9C is a perspective drawing showing the exemplary patient reference device 600 installed. FIG. 9D is a perspective drawing showing the exemplary patient reference device 600 installed with sterile draping in place. FIG. 9E is a perspective drawing showing the exemplary patient reference device 600 installed with sterile draping in place. FIGS. 9B-E are now discussed concurrently.

In FIGS. 9B-D, the patient reference device is shown attached to an arm such as the arm 500. The mounting bolt 504 of the arm 500 attaches the arm 500 to a Mayfield clamp 902, or any other suitable head holding device for restraining the head of a patient. Since the patient reference device 600 is therefore rigidly attached to the Mayfield clamp 902, the patient reference device 600 is located in a fixed location relative to the patient's head and therefore relative to the surgical site of interest.

FIGS. 9D-E show the patient reference device 600 with a sterile drape 904 attached, covering arm 500 and other components that are typically not sterilized prior to the medical procedure to be performed. Sterile cover 612 and lens 616 are also shown in position attached to the continuous edge 610 of the patient reference device 600.

In one example, the patient reference device 600 may be sold as a kit for assembly by an end user, such as a hospital or medical clinic. The kit may include the housing 602, the cover 612, the arm 500 having mounting bolt 504 or other suitable connecting mechanism for attaching to a Mayfield clamp, the tightening screw and/or knob 502, the tracking markers 608, and/or the sterile drape 904.

Figure 10:
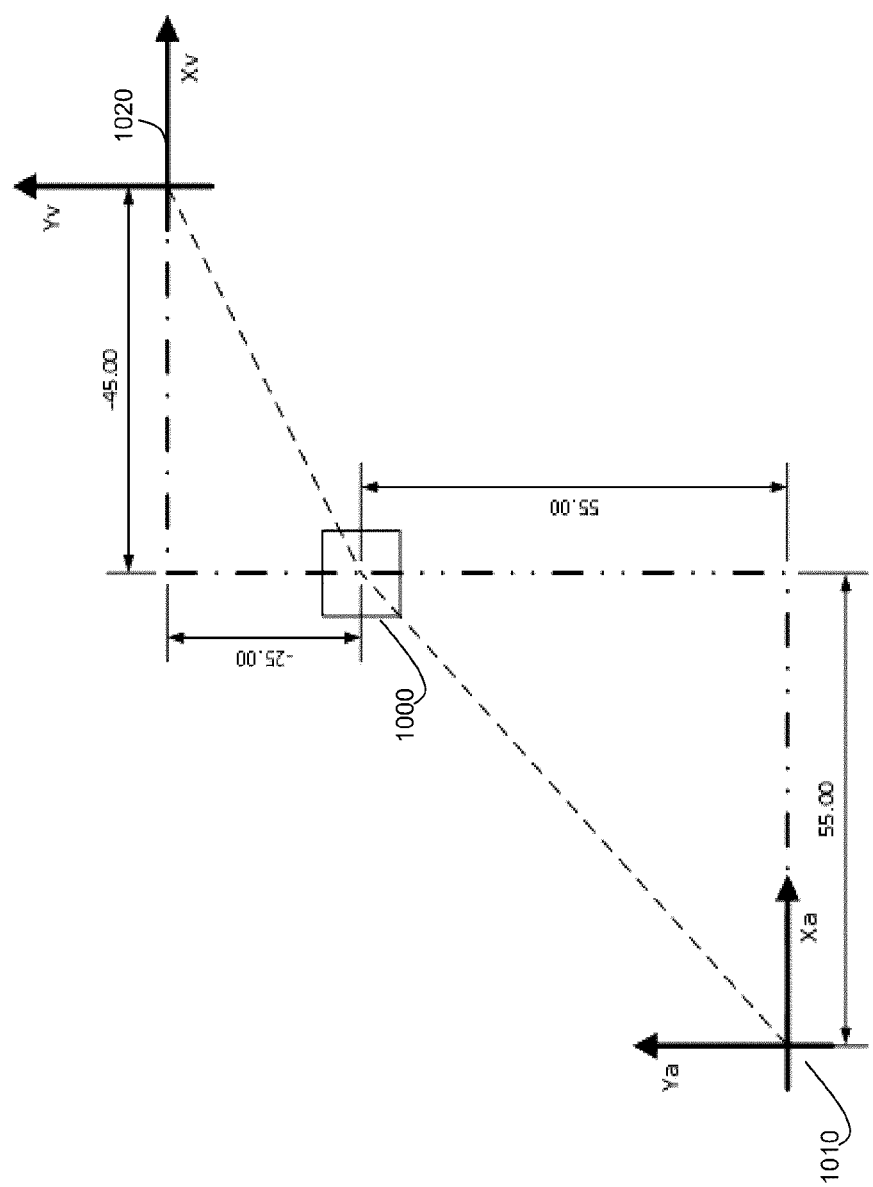
FIG. 10 illustrates a flow chart describing the use of multiple patient reference markers for registration.

Referring now to FIG. 10, a registration process, similar to that which may be used in part in block 456 of FIG. 4B, is shown for creating a common coordinate space composed of amalgamated virtual and actual coordinate spaces. The common coordinate space may be composed of both an actual coordinate space and a virtual coordinate space, where the actual coordinate space contains actual objects that exist in space and the virtual coordinate space contains virtual objects that are generated in a virtual space. The common coordinate space containing both the aforementioned actual and virtual objects may be produced as follows.

In order to form a common coordinate space composed of the amalgamated virtual and actual coordinate spaces, the two spaces may be coupled with a "common reference coordinate", having a defined position that can be located in both the actual and virtual coordinate spaces. An example of such a common reference coordinate 1000 and actual and virtual coordinate space origins, 1010 and 1020, are provided in FIG. 10. Once the common reference coordinate position is acquired in both spaces they can be used to correlate the position of any point in one coordinate space to the other. The correlation is determined by equating the locations of the common reference coordinate in both spaces and solving for an unknown translation variable for each degree of freedom defined in the two coordinate spaces. These translation variables may then be used to transform a coordinate element of a position in one space to an equivalent coordinate element of a position in the other. An example correlation can be derived from the diagram in FIG. 10 depicting a two dimensional coordinate space. In FIG. 10, the common reference coordinates 1000 position is determined relative to the actual coordinate space origin 1010 and the virtual coordinate space origin 1020. The common reference coordinates positions can be derived from the diagram as follows:

$$(X_{cra}, Y_{cra}) = (55, 55) \text{ and}$$

$$(X_{crv}, Y_{crv}) = (-25, -45)$$

Where the subscript "cra" denotes the common reference coordinate position relative to the actual coordinate space origin and the subscript "crv" denotes the common reference coordinate position relative to the virtual coordinate space origin. Utilizing a generic translation equation describing any points $((Y_a, X_a)$ and $(Y_v, X_v))$, where the subscript "a" denotes the coordinates of a point relative to the actual coordinate space origin 1010, and the subscript "v" denotes the coordinate of a point relative to the virtual coordinate space origin 1020, we can equate the individual coordinates from each space to solve for translation variables (($Y_T$, $X_T$)), where the subscript "T" denotes the translation variable as shown below.

$$Y_a = Y_v + Y_T$$

$$X_a = X_v + X_T$$

Now substituting the derived values of our points from FIG. 10 we can solve for the translation variable.

$$55 = -45 + Y_T$$

$$100 = Y_T \text{ and}$$

$$55 = -25 + X_T$$

$$80 = X_T$$

Utilizing this translation variable, any point ((i.e. ($Y_v$, $X_v$)) in the virtual coordinate space may be transformed into an equivalent point in the actual coordinate space through the two generic transformation equations provided below. It should be noted that these equations can be rearranged to transform any coordinate element of a position from the actual coordinate space into an equivalent coordinate element of a position in the virtual coordinate space as well.

$$Y_a = Y_v + 100$$

And $$X_a = X_v + 80$$

This will allow both the virtual and actual objects respective positions to therefore be defined in both the actual and virtual coordinate spaces simultaneously. Once the correlation is determined the actual and virtual coordinate spaces become coupled and result in the formation of a common coordinate space that may be used to register virtual and actual objects. It should be noted that these virtual and actual objects can be superimposed in the common coordinate space (e.g., they can occupy the same coordinates simultaneously).

According to one aspect of the present application, using a handheld three dimensional (3D) surface scanner system, such as the 3D scanner 309, a full or nearly full array scan of a patient's surface can be achieved, as opposed to 1D line or a 2D grid of point depths with the conventional approaches. This may provide an order of magnitude greater point information than the surface tracing methods used in conventional approaches. Using a dense point cloud provided by the 3D scanner 309, this point cloud may be mapped to the extracted surface of the MR/CT volumetric scan data (e.g., the pre-op image data 354) to register the patient's physical position to the volumetric data. The tracking system 321 (e.g., part of the navigation system 205) has no reference to the point cloud data. Therefore a tool may be provided that is visible to both the tracking system 321 and the 3D scanner 309. A transformation between the tracking system's camera space and the 3D scanner space may be identified so that the point cloud provided by the 3D scanner 309 and the tracking system 321 can be registered to the patient space. A transformation similar to or based on the transformation described in connection with FIG. 10 may be used.

One aspect of the present application provides a tracking tool at least partially optimized for visibility and tracking by both the tracking system 321 and a 3D scanner system, such as the 3D scanner 309. In one example, the 3D scanner 309 may be a colour 3D scanner. The 3D scanner 309 may be used to collect a colour point cloud which is defined in the patient space. To determine a transformation mapping between the tracking system 321 and the patient space, the tracking tool may be identifiable in both spaces. While there may be guidelines for tool design compatibility with the tracking system 321, no such rules exist for creating targets for extraction within point clouds. In one example, a cross-compatible tool may be designed using three retro-reflective circular targets placed at unique distances from one another on a single rigid plane. Each target may include an IR retro-reflective sphere for visibility by the tracking system 321. Three dimensional features may be provided on the tracking tool which enables straight forward extraction from the output point cloud collected from the 3D scanner 309.

Figure 11:
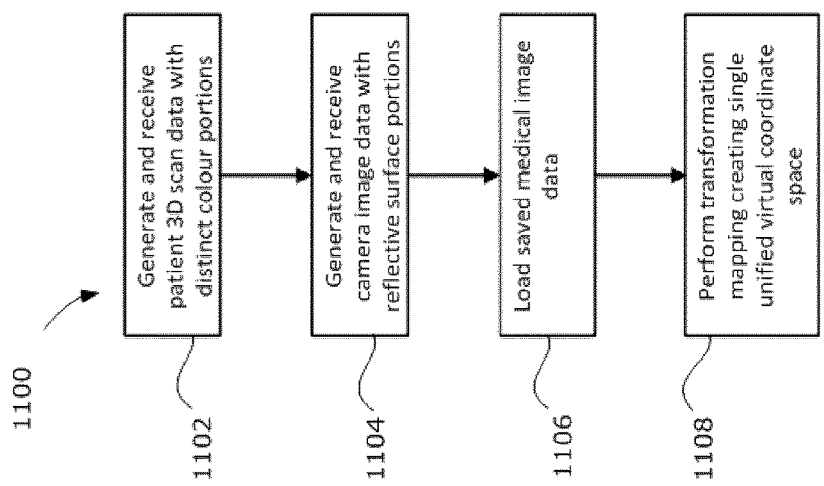
FIG. 11 is a flow chart illustrating a method of registering a patient for a medical procedure with a medical navigation system using a patient reference device.

Referring now to FIG. 11, a flow chart is shown illustrating a method 1100 of registering a patient for a medical procedure with a medical navigation system using a patient reference device, such as the patient reference device 1300 discussed below in connection with FIG. 13. The method 1100 may register a patient for a medical procedure with a medical navigation system, such as the medical navigation system 205, using a patient reference device (e.g., the apparatus 600 or the patient reference device 1300) visible by both a three dimensional (3D) scanner system (e.g., including the 3D scanner 309) of the medical navigation system 205 and a camera (e.g., the camera 307) of the medical navigation system 205. The method may be controlled and/or executed, for example by the processor 302 of the control and processing unit 300 that forms part of the medical navigation system 205.

At a first block 1102, the method 1100 generates and receives 3D scan data from the 3D scanner 309 that is representative of a 3D scan of at least a portion of the patient 202. The 3D scan includes distinct identifiable portions of the patient reference device 1300 that are visible by the 3D scanner 309. In one example, the distinct identifiable portions may be one or more 3D shapes located on a surface of the patient reference device 1300. In another example, the distinct identifiable portions may be three dimensional indicators or distinct color portions. While this is provided as an example, the scan data need not be 3D scanned data with distinct color portions and other suitable forms of data may be used.

Next, at a block 1104, the method 1100 generates and receives image data from the camera 307. In one example, the image data may include reflective surface portions of the patient reference device 1300 visible by the camera 307. In one example, the reflective surface portions may be the reflective markers 1304 (FIG. 13). While reflective markers are used as an example, any suitable type of markers may be used according to the design criteria of a particular application.

Next, at a block 1106, the method 1100 loads saved medical image data. The saved medical data includes pre-operative image data, such as the pre-op image data 354, saved during a previous scan of at least a portion of the patient 202. The pre-op image data 354 may include data from computerized tomography (CT) images, magnetic resonance imaging (MRI) images, positron emission topography (PET) images, contrast-enhanced CT images, X-ray images, ultrasound images, or any other suitable medical imaging source.

While the blocks 1102, 1104, and 1106 are shown as being performed in a particular order, blocks 1102, 1104, and 1106 may be performed in any suitable order, including concurrently.

Next, at a block 1108, the method 1100 performs a transformation mapping to create a single unified virtual coordinate space based on the 3D scan data, the image data, and the medical image data. In one example, the transformation may be similar to or based on the registration process described in connection with FIG. 10. In another example, the transformation mapping includes a surface matching approach using a 3D scanner point cloud based on the 3D scan data and at least one of MR and CT coordinates. In another example, the camera 307 of the medical navigation system 205 may form part of a tracking system, such as the tracking system 321, and the transformation mapping may further include registering the tracking system 321 to create a single unified virtual coordinate space for the 3D scanner point cloud, at least one of the MR and CT coordinates, and the image data from the tracking system. However any suitable known or yet to be developed transformation process may be applied.

While the blocks of FIG. 11 are shown in a particular order for the purpose of example, the blocks 1102, 1104, 1106, and 1108 need not be executed in the exact order shown and suitable modifications may be made to this order, an example of which is shown below in connection with FIG. 12.

Figure 12:
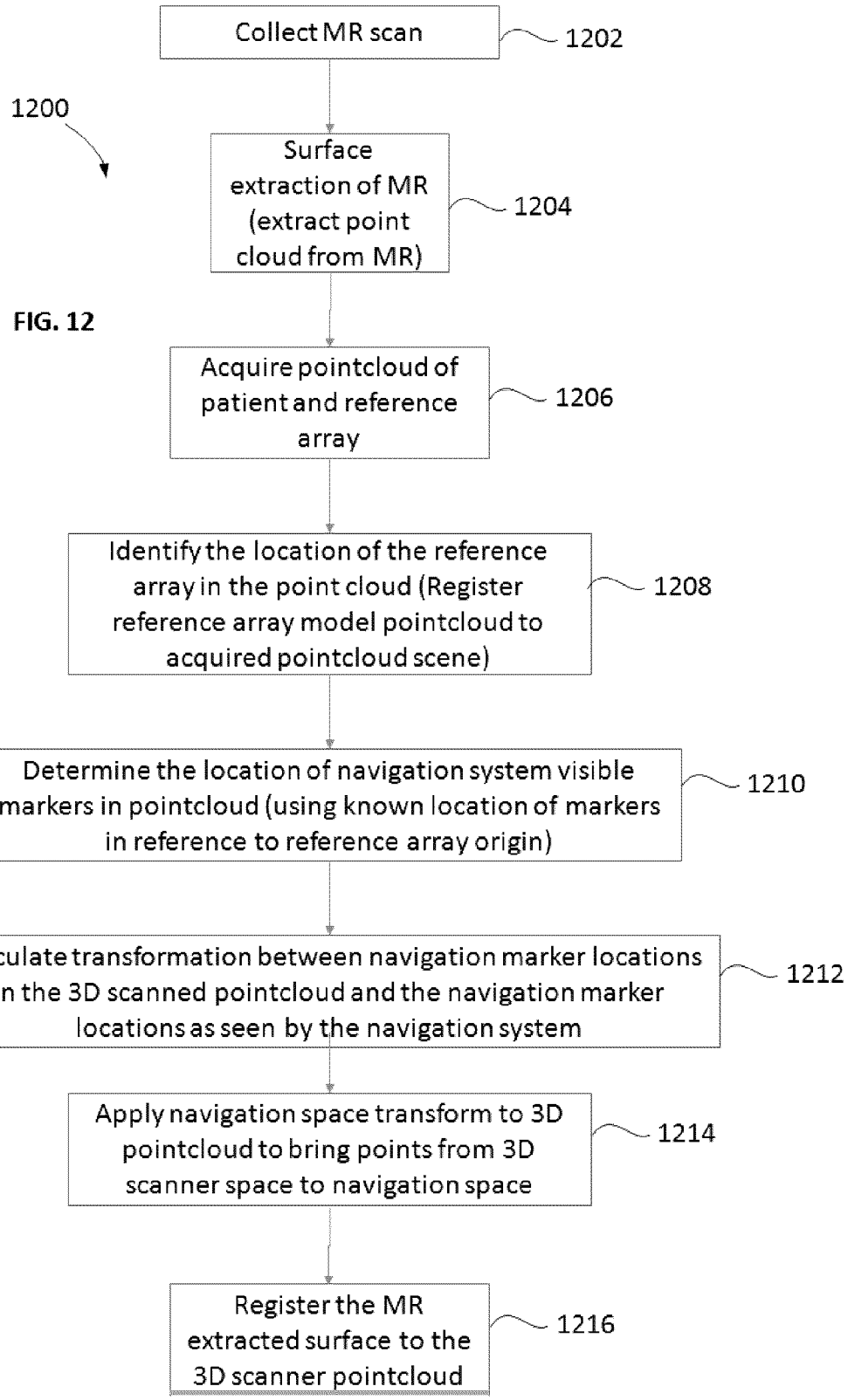
FIG. 12 is another flow chart illustrating a method of registering a patient for a medical procedure with a medical navigation system using a patient reference device.

Referring now to FIG. 12, another flow chart is shown illustrating another example method 1200 of registering a patient for a medical procedure with a medical navigation system, similar to the method 1100 discussed in connection with FIG. 11.

At a first block 1202, image scan data is collected. The collected image scan data may be similar to the saved medical image data loaded at block 1106 of method 1100. The image scan data could include any 3D volumetric image scan data such as magnetic resonance (MR) image scan data, CT image scan data, 3D ultrasound image scan data, or any other suitable type of scanned image data according to the design criteria of a particular application.

Next, at a block 1204, a surface extraction is performed from the image scan data to generate a point cloud, which may be part of the transformation mapping performed at block 1108 in method 1100.

Next, at a block 1206, a point cloud of the patient and reference array (e.g., the apparatus 1300) may be generated. The point cloud generation may be performed using data generated by the handheld 3D scanner 309.

Next, at a block 1208, the location of the reference array in the point cloud is identified. In one example, the medical navigation system 205 may have stored data that allows the system to recognize the reference array, such as the patient reference device 1300, in an image scanned by the 3D scanner 309. In one example, the reference array may have three dimensional features that are recognizable in an image scanned by the 3D scanner 309, allowing the medical navigation system 205 to find the reference array in the image because the 3D features are in known locations in reference to some features, such as reflective markers, that can be seen by the navigation system.

Next, at a block 1210, the location of the navigation system visible markers may be determined in the point cloud. In one example, once the medical navigation system has determined the location of the reference array (e.g., at block 1208), finding the visible markers on the reference array may be a fairly simple task since the reference array has a spatial configuration known by the medical navigation system 205.

Next, at a block 1212, the transformation between the navigation marker locations in the 3D scanned point cloud and the navigation marker locations seen by the navigation system may be calculated.

Next, at a block 1214, the navigation space transform may be applied to the 3D point cloud to bring points from the 3D scanner 309 space into the navigation space.

Finally, at a block 1216, the patient image extracted surface is registered to the 3D scanner 309 point cloud. Blocks 1212, 1214, and 1216 may be similar to and/or part of block 1108 performed in method 1100. In one example, the methods 1100 and/or 1200 may employ an Iterative Closest Point (ICP) approach to calculate the registration transformation, such as that detailed in "A Method for Registration of 3-D Shapes" by Paul J. Besl and Neil D. McKay, IEEE Transactions on Pattern Analysis and Machine Intelligence, pp. 239-256, VOL. 14, No. 2, February 1992, the entirety of which is hereby incorporated by reference. However, any suitable approach may be used depending on the design criteria of a particular application.

The method 1100 shown in FIG. 11 and method 1200 shown in FIG. 12 are shown as an example to illustrate the context of the patient reference device 1300, which is described in more detail below in connection with FIG. 13.

Figure 13:
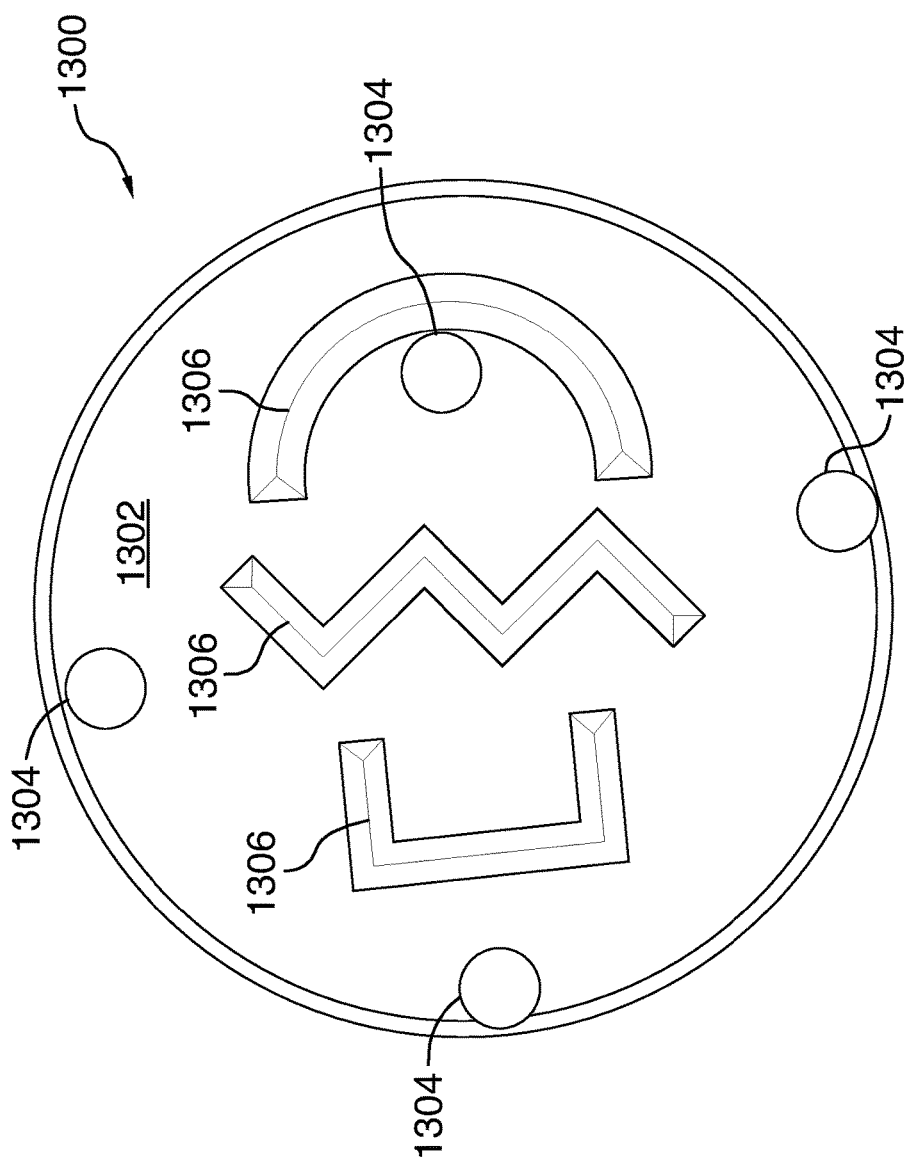
FIG. 13 is a top view of a patient reference device similar to the device shown in FIG. 6.

Referring now to FIG. 13, a top view of an apparatus 1300 is shown. In one example, the apparatus 1300 may be referred to as a patient reference tool or patient reference device similar to the device 600 shown in FIG. 7. In one example, the patient reference device may be used during a medical procedure. The apparatus 1300 may be visible by both the three dimensional (3D) scanner system 309 of the medical navigation system 205 and the tracking system 321 of the medical navigation system 205. In one example, a camera 307 of the tracking system 321 may be used to see the apparatus 1300. The apparatus 1300 has a rigid member 1302 and a plurality of navigation system visible identifiable features that are attached to the rigid member 1302. In one example, the navigation system identifiable features are reflective markers 1304. The plurality of reflective markers 1304 is visible by the tracking system 321, for example by the camera 307. The apparatus 1300 further has a distinct identifiable portion 1306 visible by the 3D scanner system 309 and a connector mechanism attached to the rigid member 1302 to connect the apparatus to a location. The connector mechanism is not shown in FIG. 13, but may be similar to the mechanisms described in connection with FIGS. 5 and 9A-E. The apparatus 1300 may be in a field of view of the 3D scanner system 309 and the tracking system 321 within a timeframe of the 3D scan. In one example, the identifiable features include reflective markers 1304 and the tracking system 321 includes the camera 307. In another example, the identifiable features may include magnetic coils and the tracking system may include magnetic tracking sensors. In further alternate embodiments, the identifiable features may also include RFID tags or barcode tags and the tracking system includes a RFID scanner or a barcode scanner. Similar to reflective markers, RFID and barcode tags can be programmed with location data which when read from a respective RFID or barcode scanner can transfer scanned data to the navigation system.

In one example, the apparatus 1300 has at least three reflective markers 1304 mounted on a front side of the rigid member 1302. However, any suitable number of reflective markers 1304 may be used to meet the design criteria of a particular application. In one example, the tracking markers 1304 may be passive reflective tracking spheres, active infrared markers, active light emitting diodes, a graphical pattern, or any other suitable type of markers.

In another example, the rigid member 1302 may be substantially rigid and/or planar in shape and may have a thickness or depth to the rigid member 1302 sufficient to accommodate the desired depth of the distinct identifiable portion 1306. The distinct identifiable portion 1306 may include a three dimensional indicator formed on the front side of the rigid member 1302. In another example, the distinct identifiable portion 1306 may include a three dimensional indicator formed on the back side of the rigid member 1302. In another example, the distinct identifiable portion 1306 may include a three dimensional indicator formed on both the back side and the front side of the rigid member 1302. The three dimensional indicator may either be engraved or etched in the rigid member 1302 or the three dimensional indicator may be formed of a raised surface portion on the front side of the rigid member 1302. In the example shown in FIG. 13, the three dimensional indicator 1306 includes three separate unique indicators, indicated by reference 1306, however any suitable number of three dimensional indicators may be used to meet the design criteria of a particular application. While rigid member 1302 is described, in one example, as planar and having a front side and a backside, any suitable three dimensional shape may be used for rigid member 1302. For example, rigid member 1302 could be in the shape of a sphere, cone, pyramid, cube, prism, or even an amorphous shape.

In another embodiment, the apparatus 1300 may be a patient reference device. The rigid member 1302 may be referred to as a housing having a back side and a front side with a plurality of tracking markers 1304 attached to the front side of the housing. The apparatus 1300 may have a distinct identifiable portion 1306 including a three dimensional indicator formed on the front side of the housing. The housing extends around the plurality of tracking markers 1304 and beyond a horizontal plane defined by tops of the plurality of tracking markers 1304. The housing terminates at a substantially continuous edge. A sterile cover may be attached to the substantially continuous edge of the housing for covering the housing and the tracking markers 1304, similar to patient reference device 600.

The apparatus 1300 may further have a strap connected to the rigid member 1302 for securing the apparatus 1300 to a patient. In one example, the strap is attachable around a head of the patient. In another example, the apparatus 1300 is securable to a patient using a medical adhesive. The timeframe may be at least one frame of the 3D scan and the field of view may include the patient reference with the scanning range of the 3D scanner 309 including the head of the patient.

The reference location may be a fixed location such that the rigid member is attachable on a Mayfield head clamp, a bed, or a stretcher and the connector mechanism may be attached to a back side of the rigid member 1302. In another example, the reference location includes being attached onto a patient, rested on the skin of the patient, and the apparatus 1300 may be wearable. The apparatus 1300 may further be sterilizable and/or disposable. While some examples are provided of how apparatus 1300 may be constructed or mounted, apparatus 1300 may have any of the characteristics described in connection with patient reference device 600 described in connection with FIGS. 6-9 depending on the design criteria of a particular application.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

We claim:

1. A patient reference device for use during a medical procedure, the patient reference device comprising:
   a housing having a back side and a front side;
   a plurality of tracking markers attached to the front side of the housing;
   a three dimensional indicator formed on the front side of the housing;
   the housing extending around the plurality of tracking markers and beyond a horizontal plane defined by tops of the plurality of tracking markers, the housing terminating at a continuous edge; and
   a sterile cover attached to the continuous edge of the housing for covering the housing and the tracking markers.

2. The patient reference device according to claim 1, wherein the housing is attachable to a patient reference arm that is attachable to a Mayfield head clamp.

3. The patient reference device according to claim 1, wherein there are at least three tracking markers attached to the front side of the housing.

4. The patient reference device according to claim 1, wherein the tracking markers are selected from the group consisting of passive reflective tracking spheres, active infrared markers, active light emitting diodes, and a graphical pattern.

5. The patient reference device according to claim 1, wherein the three dimensional indicator is engraved on the front side of the housing.

6. The patient reference device according to claim 1, wherein the three dimensional indicator includes a raised surface portion on the front side of the housing.

7. The patient reference device according to claim 1, wherein the three dimensional indicator includes at least three separate unique indicators.

8. An apparatus, at least partly visible by both a three dimensional (3D) scanner system of a medical navigation system and a tracking system of the medical navigation system, the apparatus comprising:
   a rigid member attachable to a location;
   a plurality of tracking markers attached to a front side of the rigid member and visible by the tracking system;
   a three dimensional indicator formed on the front side of the rigid member and visible by the 3D scanner system;
   the rigid member extending around the plurality of tracking markers and beyond a horizontal plane defined by tops of the plurality of tracking markers, the rigid member terminating at a continuous edge; and
   a sterile cover attached to the rigid member for covering the rigid member and the tracking markers,
   wherein the apparatus is to be in a field of view of both the 3D scanner system and the tracking system during a timeframe of a 3D scan by the 3D scanner.

9. The apparatus according to claim 8, wherein the tracking markers include reflective markers attached to the front side of the rigid member.

10. The apparatus according to claim 8, wherein the rigid member is planar in shape.

11. The apparatus according to claim 8, wherein the three dimensional indicator includes a three dimensional graphical pattern formed on the rigid member.

12. The apparatus according to claim 11, wherein the three dimensional graphical pattern is at least one of engraved and etched in the rigid member.

13. The apparatus according to claim 11, wherein the three dimensional graphical pattern includes a raised surface portion on the rigid member.

14. The apparatus according to claim 8, wherein the apparatus further comprises:
   a strap connected to the rigid member for securing the apparatus to a patient.

15. The apparatus according to claim 14, wherein the strap is attachable around a head of the patient.

16. The apparatus according to claim 8, wherein the apparatus is securable to a patient using a medical adhesive.

17. The apparatus according to claim 8, wherein the timeframe is at least one frame of the 3D scan.

18. The apparatus according to claim 8, wherein the location is a reference location comprising at least one of a fixed location on a Mayfield clamp, a bed, and a stretcher.

19. The apparatus according to claim 18, wherein the reference location includes being attached onto a patient.

20. The apparatus according to claim 8, wherein the apparatus is wearable.

21. The apparatus according to claim 8, wherein the apparatus is sterilisable.

22. The apparatus according to claim 8, wherein the field of view includes a patient reference.

23. The apparatus according to claim 8, wherein the rigid member is spherical in shape.

\* \* \* \* \*